(12) United States Patent
Coats et al.

(10) Patent No.: US 8,895,573 B2
(45) Date of Patent: Nov. 25, 2014

(54) PHENOXY-SUBSTITUTED PYRIMIDINES AS OPIOID RECEPTOR MODULATORS

(71) Applicant: Janssen Pharmaceutica, NV, Beerse (BE)

(72) Inventors: Steven J Coats, McDonough, GA (US); Yue-Mei Zhang, Spring House, PA (US); Shu-Chen Lin, Doylestown, PA (US); Li Liu, Germantown, MD (US); Tamara A Miskowski, Chalfont, PA (US); Scott L. Dax, Landenberg, PA (US); Henry J Breslin, Lansdale, PA (US); Bart L. De Corte, Southampton, PA (US); Wei He, Audubon, PA (US)

(73) Assignee: Janssen Pharmaceutica, NV (BE)

( * ) Notice: Subject to any disclaimer, the term of this patent is extended or adjusted under 35 U.S.C. 154(b) by 0 days.

(21) Appl. No.: 13/766,046

(22) Filed: Feb. 13, 2013

(65) Prior Publication Data

US 2014/0066422 A1    Mar. 6, 2014

Related U.S. Application Data

(62) Division of application No. 12/913,948, filed on Oct. 28, 2010, now Pat. No. 8,394,809.

(60) Provisional application No. 61/256,394, filed on Oct. 30, 2009.

(51) Int. Cl.
| | |
|---|---|
| *A01N 43/54* | (2006.01) |
| *A61K 31/505* | (2006.01) |
| *C07D 401/12* | (2006.01) |
| *A61K 31/506* | (2006.01) |
| *C07D 417/12* | (2006.01) |
| *C07D 403/12* | (2006.01) |
| *C07D 413/12* | (2006.01) |
| *C07D 239/28* | (2006.01) |
| *C07D 239/52* | (2006.01) |
| *C07D 239/34* | (2006.01) |

(52) U.S. Cl.
CPC ............ *C07D 239/52* (2013.01); *C07D 401/12* (2013.01); *A61K 31/506* (2013.01); *C07D 417/12* (2013.01); *C07D 403/12* (2013.01); *C07D 413/12* (2013.01); *C07D 239/28* (2013.01); *C07D 239/34* (2013.01)
USPC ........... 514/269; 514/272; 514/274; 544/310; 544/311; 544/319

(58) Field of Classification Search
USPC ............ 544/30, 311, 319, 320; 514/269, 272, 514/274
See application file for complete search history.

(56) References Cited

U.S. PATENT DOCUMENTS

| 6,465,467 B1 | 10/2002 | Nilsson et al. |
|---|---|---|
| 7,015,227 B2 | 3/2006 | Darrow et al. |
| 7,071,180 B2 | 7/2006 | Nilsson et al. |
| 7,534,794 B2 | 5/2009 | Nilsson et al. |
| 2003/0199511 A1 | 10/2003 | Li et al. |
| 2006/0142307 A1 | 6/2006 | Hellberg et al. |
| 2009/0264474 A1 | 10/2009 | Branum et al. |

FOREIGN PATENT DOCUMENTS

| CN | 1628103 A | | 7/2002 |
|---|---|---|---|
| CN | 1628103 A | * | 6/2005 |
| WO | 00/76984 | | 12/2000 |
| WO | 02/08205 A1 | | 1/2002 |
| WO | 02/42280 A2 | | 5/2002 |
| WO | 03/051366 A3 | | 6/2003 |
| WO | 2004/000318 A2 | | 12/2003 |
| WO | 2004/071426 A2 | | 8/2004 |
| WO | 2008/046226 A1 | | 4/2008 |

OTHER PUBLICATIONS

F. Curd et al., Journal of the Chemical Society (1946) 378-384.*
C. Stein, et al., 93 Current Opinion in Pharmacology, 3-8 (2009).*
L. Gendron et al., 150 Neuroscience, 807-817 (2007).*
Evans, C.J.(1993), "Diversity Among the Opioid Receptors", in Biological Basis of Substance Abuse, eds. Korenman SG and Barchas J.D. (Oxford University Press, New York), p. 31-48.
Gilbert, P. E. & Martin, W. R., "The Effects of Morphine- and Nalorphine-Like Drugs in the Nondependent, Morphine-Dependent and Cyclazocine-Dependent Chronic Spinal Dog", *J Pharmacol Exp Ther*, 1976, vol. 198, p. 66-82.
Gross, R.A., et al., "Dynorphin A and cAMP-dependent protein kinase independently regulate neuronal calcium currents", *Proc Natl Acad Sci USA*, 1990, vol. 87, p. 7025-7029.
Lord, J. A., et al., "Endogenous opioid peptides: multiple agonists and receptors", *Nature*, 1977, vol. 267, p. 495-499.
Mansour, a., et al., "Anatomy of CNS Opioid Receptors", *Trends in Neurosci*, 1988, vol. 11, p. 308-314.
Pert, C. B. And Snyder, S. H., "Opiate Receptor: Demonstration in Nervous Tissue", Science (1973) 179:1011-1014.

(Continued)

*Primary Examiner* — James O. Wilson
*Assistant Examiner* — Alexander R Pagano

(57) ABSTRACT

Disclosed are compounds, compositions and methods for treating various diseases, syndromes, conditions and disorders, including pain. Such compounds are represented by Formula I as follows:

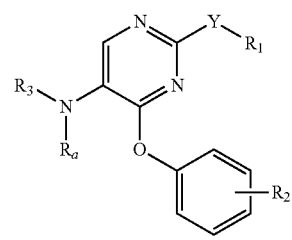

Formula I wherein $R_1$, Y, $R_2$, $R_3$, and $R_a$ are defined herein.

3 Claims, No Drawings

(56) References Cited

OTHER PUBLICATIONS

Sharma, S. K., et al., "Dual regulation of adenylate cyclase accounts for narcotic dependence and tolerance" *Proc Natl Acad Sci USA*, 1975, vol. 72, p. 3092-3096.

Wollemann, M., "Recent Developments in the Research of Opioid Receptor Subtype Molecular Characterization", *J Neurochem*, 1990, vol. 54, p. 1095-1101.
International Search Report and Written Opinion, PCT/US2010/054478, dated Jan. 21, 2011.

* cited by examiner

PHENOXY-SUBSTITUTED PYRIMIDINES AS OPIOID RECEPTOR MODULATORS

CROSS REFERENCE TO RELATED APPLICATIONS

The present application is a divisional application of U.S. application Ser. No. 12/913,948 filed Oct. 28, 2010 which claims the benefits of the filing of U.S. Provisional Application No. 61/256,394, filed on Oct. 30, 2009. The complete disclosures of the aforementioned related patent applications are hereby incorporated herein by reference for all purposes.

FIELD OF THE INVENTION

The present invention is directed to novel opioid receptor modulators of Formula (I). The invention further relates to methods for preparing such compounds, pharmaceutical compositions containing them, and their use in the treatment of opioid modulated disorders.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

There is a continuing need for new opioid receptor modulators as analgesics. There is a further need for delta and mu opioid receptor agonists as analgesics having reduced side effects. There is a further need for mu opioid receptor agonists as analgesics having reduced side effects for the treatment of pain, immune function, esophageal reflux, and cough. There is also a need for delta opioid receptor agonists as analgesic agents, agents for the treatment of respiratory diseases, cardiovascular agents, agents for treating urological dysfunction, and agents for the treatment of neurological and psychiatric conditions. There is further need for dual delta opioid receptor/mu opioid receptor agonists.

SUMMARY OF THE INVENTION

The present invention is directed to compounds of Formula (I)

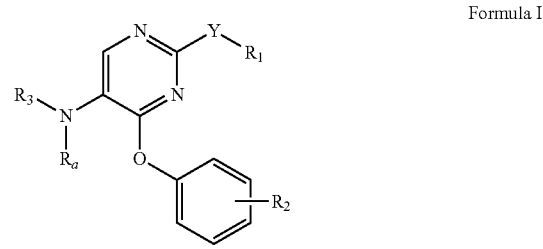

Formula I wherein
$R_1$ is selected from the group consisting of phenyl, pyridinyl, and thiazolyl; wherein $R_1$ is optionally substituted with one to two substituents independently selected from the group consisting of $C_{1-4}$alkyl, $C_{1-4}$alkoxy, $C_{1-4}$alkylthio, hydroxy, fluoro, chloro, bromo, and cyano; in addition, $R_1$ is optionally substituted with amino, $C_{1-4}$alkylamino, di($C_{1-4}$alkyl)amino, aminocarbonyl, $C_{1-4}$alkylaminocarbonyl, or di($C_{1-4}$alkyl)aminocarbonyl;

Y is O, S, NH, vinyl, ethynyl or S(O);

$R_2$ is a substituent selected from the group consisting of hydrogen, $C_{1-4}$alkyl, $C_{1-4}$alkoxy, $C_{1-4}$alkylthio, fluoro, chloro, bromo, and hydroxy;

$R_a$ is hydrogen or methyl;

$R_3$ is selected from the group consisting of pyrrolidin-2-ylmethyl, pyrrolidin-3-ylmethyl, piperidin-2-ylmethyl, piperidin-3-ylmethyl, piperidin-4-ylmethyl, piperidin-2-ylethyl, piperidin-3-ylethyl, piperidin-4-ylethyl, pyridin-4-yl-($C_{1-2}$)alkyl, azetidin-3-ylmethyl, morpholin-2-ylmethyl, morpholin-3-ylmethyl, imidazolylmethyl, thiazolylmethyl, (amino)-$C_{3-6}$cycloalkyl, 3-hydroxy-2-amino-propyl, 8-aza-bicyclo[3.2.1]octanyl, 1-aza-bicyclo[2.2.2]octanyl, guanidinyl-ethyl, 4-(imidazol-1-yl)phenylmethyl, 2-(methylamino)-ethyl, 2-diethylamino-ethyl, 4-diethylamino-but-2-yl, piperidin-3-yl, piperidin-4-yl, and pyrrolidin-3-yl;

and wherein piperidin-3-yl is optionally substituted at a carbon atom with phenyl; and wherein pyrrolidin-2-yl of pyrrolidin-2-ylmethyl, pyrrolidin-3-yl, piperidin-3-yl, and piperidin-4-yl are optionally substituted at a nitrogen atom with methyl, phenylmethyl, phenethyl, or methylcarbonyl;

and enantiomers, diastereomers, solvates, and pharmaceutically acceptable salts thereof.

The present invention is also directed to a pharmaceutical composition comprising a pharmaceutically acceptable carrier and a compound of Formula (I) or a pharmaceutically acceptable salt form thereof.

Also provided are processes for making a pharmaceutical composition comprising mixing a compound of Formula (I) and a pharmaceutically acceptable carrier.

The present invention is further directed to methods for treating or ameliorating an opioid receptor-modulated disorder. In particular, the methods of the present invention are directed to treating or ameliorating a opioid receptor-modulated disorder including, but not limited to, inflammatory pain, centrally mediated pain, peripherally mediated pain, visceral pain, structural related pain, cancer/pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine.

The present invention also provides methods for producing the instant compounds and pharmaceutical compositions and medicaments thereof.

As used herein, the following terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

With reference to substituents, the term "independently" means that when more than one of such substituent is possible, such substituents may be the same or different from each other. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as ($C_{1-6}$alkyl)$_2$amino-the $C_{1-6}$alkyl groups of the dialkylamino may be the same or different.

"Halogenated alkyl" refers to a saturated branched or straight chain alkyl radical derived by removal of 1 hydrogen atom from the parent alkane; the parent alkyl chain contains from 1 to 8 carbon atoms with 1 or more hydrogen atoms replaced with halogen atoms up to and including replacement of all hydrogen atoms with halogen. Preferred halogenated alkyl groups include trifluoromethyl substituted alkyls, difluoromethyl substituted alkyls, and perfluorinated alkyls; more preferred fluorinated alkyls include trifluoromethyl and difluoromethyl.

"Halogenated alkoxy" refers to a radical derived from a halogenated alkyl, radical attached to an oxygen atom with the oxygen atom having one open valence for attachment to a parent structure.

The term "cycloalkyl" refers to saturated or partially unsaturated, moncyclic or polycyclic hydrocarbon of from 3 to 20 carbon atom members (preferably from 3 to 14 carbon atom members). Examples of such groups include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), or a 5 or 6 membered heteroaryl ring (containing one of O, S or N and, optionally, one additional nitrogen) to form a heteroaryl fused cycloalkyl.

The term "heterocyclyl" refers to a nonaromatic monocyclic ring of 5 to 10 members in which 1 to 4 members are nitrogen or a nonaromatic monocyclic ring of 5 to 10 members in which zero, one or two members are nitrogen and up to two members are oxygen or sulfur; wherein, optionally, the ring contains zero, one or two unsaturated bonds. The term heterocyclyl includes a heterocyclyl ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzofused heteroaryl), a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinoxalinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

The term "vinyl" refers to a two-carbon unsaturated linker in which the unsaturation is a double bond between said two carbon atoms. When two substituents occur on the vinyl linker, the substituents are to be bound on adjacent carbon atoms, such that the substituents are 1,2-configured.

The term "oxo" whether used alone or as part of a substituent group refers to an O= to either a carbon or a sulfur atom. For example, phthalimide and saccharin are examples of compounds with oxo substituents.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "acyl" refers to alkylcarbonyl substituents.

Throughout this disclosure, the terminal portion of the designated side chain is described first, followed by the adjacent functionality toward the point of attachment. Thus, for example, a "phenyl($C_{1-6}$)alkylaminocarbonyl($C_{1-6}$)alkyl" substituent refers to a group of the formula

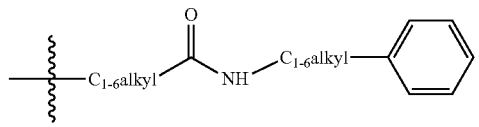

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

For purposes of the present invention, the term "opioid receptor-modulated" is used to refer to the condition of being affected by the modulation of an opioid receptor, including but not limited to, the state of being mediated by the opioid receptor.

DETAILED DESCRIPTION OF THE INVENTION

Embodiments of the present invention include those compounds of Formula (I) wherein
a) $R_1$ is selected from the group consisting of phenyl, pyridinyl, and thiazolyl; wherein $R_1$ is optionally substituted with one to two substituents independently selected from the group consisting of $C_{1-4}$alkoxy, fluoro, chloro, bromo, and cyano; in addition, $R_1$ is optionally substituted with aminocarbonyl, $C_{1-4}$alkylaminocarbonyl, or di($C_{1-4}$alkyl)aminocarbonyl;
b) $R_1$ is phenyl optionally substituted with one to two substituents independently selected from the group consisting of $C_{1-4}$alkoxy, fluoro, and bromo; in addition, $R_1$ is optionally substituted with di($C_{1-4}$alkyl)aminocarbonyl;
c) $R_1$ is phenyl optionally substituted with one to two substituents independently selected from the group consisting of $C_{1-4}$alkoxy and fluoro; in addition, $R_1$ is optionally substituted with di($C_{1-4}$alkyl)aminocarbonyl;
d) $R_1$ is phenyl optionally substituted with one substituent selected from the group consisting of $C_{1-4}$alkoxy and di($C_{1-4}$alkyl)aminocarbonyl;
e) Y is O, NH, vinyl, ethynyl, or S(O),
f) Y is O or ethynyl;
g) Y is O;
h) $R_2$ is a substituent selected from the group consisting of $C_{1-2}$alkoxy, fluoro, and bromo;
i) $R_2$ is $C_{1-2}$alkoxy or fluoro;
j) $R_a$ is hydrogen;
k) $R_3$ is selected from the group consisting of pyrrolidin-2-ylmethyl, pyrrolidin-3-ylmethyl, piperidin-2-ylmethyl, piperidin-3-ylmethyl, piperidin-4-ylmethyl, piperidin-3-ylethyl, piperidin-4-ylethyl, azetidin-3- ylmethyl, morpholin-2-ylmethyl, piperidin-3-yl, piperidin-4-yl, pyrrolidin-3-yl, 3-amino-cyclohexyl, 4-amino-cyclohexyl, 3-hydroxy-2-amino-propyl, 4-diethylamino-but-2-yl, 8-aza-bicyclo[3.2.1]octanyl, 1-aza-bicyclo[2.2.2]octanyl, and 2-(methylamino)-ethyl;

wherein piperidin-3-yl is optionally substituted at a carbon atom with phenyl; and wherein pyrrolidin-2-yl of pyrrolidin-2-ylmethyl, pyrrolidin-3-yl, piperidin-3-yl, and piperidin-4-yl are optionally substituted at a nitrogen atom with methyl, phenylmethyl, phenethyl, or methylcarbonyl;

l) R₃ is selected from the group consisting of pyrrolidin-2-ylmethyl, pyrrolidin-3-ylmethyl, piperidin-2-ylmethyl, piperidin-3-ylmethyl, piperidin-4-ylmethyl, azetidin-3-ylmethyl, piperidin-3-yl, piperidin-4-yl, 3-amino-cyclohexyl, 4-amino-cyclohexyl, 3-hydroxy-2-amino-propyl, 4-diethylamino-but-2-yl, 8-aza-bicyclo[3.2.1]octanyl, 1-aza-bicyclo[2.2.2]octanyl, and 2-(methylamino)-ethyl;

wherein pyrrolidin-2-yl of pyrrolidin-2-ylmethyl is optionally substituted at a nitrogen atom with methyl;

m) R₃ is selected from the group consisting of pyrrolidin-2-ylmethyl, piperidin-3-yl, and 3-amino-cyclohexyl;

wherein pyrrolidin-2-yl of pyrrolidin-2-ylmethyl is optionally substituted at a nitrogen atom with methyl;

and any combination of embodiments a) through m) above, provided that it is understood that combinations in which different embodiments of the same substituent would be combined are excluded;

and enantiomers, diastereomers, solvates, and pharmaceutically acceptable salts thereof.

A further embodiment of the present invention is directed to a compound of Formula (I)

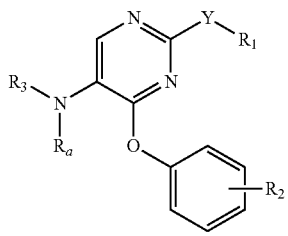

Formula (I)

wherein

R₁ is selected from the group consisting of phenyl, pyridinyl, and thiazolyl; wherein R₁ is optionally substituted with one to two substituents independently selected from the group consisting of $C_{1-4}$alkoxy, fluoro, chloro, bromo, and cyano; in addition, R₁ is optionally substituted with aminocarbonyl, $C_{1-4}$alkylaminocarbonyl, or di($C_{1-4}$alkyl)aminocarbonyl;

Y is O, NH, vinyl, ethynyl, or S(O);

R₂ is a substituent selected from the group consisting of $C_{1-2}$alkoxy, fluoro, and bromo;

$R_a$ is hydrogen or methyl;

R₃ is selected from the group consisting of pyrrolidin-2-ylmethyl, pyrrolidin-3-ylmethyl, piperidin-2-ylmethyl, piperidin-3-ylmethyl, piperidin-4-ylmethyl, piperidin-3-ylethyl, piperidin-4-ylethyl, azetidin-3-ylmethyl, morpholin-2-ylmethyl, piperidin-3-yl, piperidin-4-yl, pyrrolidin-3-yl, 3-amino-cyclohexyl, 4-amino-cyclohexyl, 3-hydroxy-2-amino-propyl, 4-diethylamino-but-2-yl, 8-aza-bicyclo[3.2.1]octanyl, 1-aza-bicyclo[2.2.2]octanyl, and 2-(methylamino)-ethyl;

wherein piperidin-3-yl is optionally substituted at a carbon atom with phenyl; and wherein pyrrolidin-2-yl of pyrrolidin-2-ylmethyl, pyrrolidin-3-yl, piperidin-3-yl, and piperidin-4-yl are optionally substituted at a nitrogen atom with methyl, phenylmethyl, phenethyl, or methylcarbonyl and enantiomers, diastereomers, solvates, and pharmaceutically acceptable salts thereof.

Another embodiment of the present invention is directed to a compound of Formula (I)

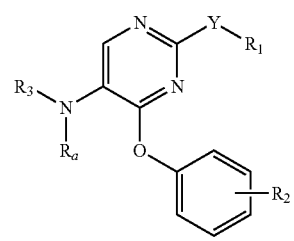

Formula (I)

wherein

R₁ is phenyl optionally substituted with one to two substituents independently selected from the group consisting of $C_{1-4}$alkoxy, fluoro, and bromo; in addition, R₁ is optionally substituted with di($C_{1-4}$alkyl)aminocarbonyl;

Y is O, NH, vinyl, ethynyl, or S(O);

R₂ is selected from the group consisting of $C_{1-2}$alkoxy, fluoro, and bromo;

$R_a$ is hydrogen;

R₃ is selected from the group consisting of pyrrolidin-2-ylmethyl, pyrrolidin-3-ylmethyl, piperidin-2-ylmethyl, piperidin-3-ylmethyl, piperidin-4-ylmethyl, azetidin-3-ylmethyl, piperidin-3-yl, piperidin-4-yl, 3-amino-cyclohexyl, 4-amino-cyclohexyl, 3-hydroxy-2-amino-propyl, 4-diethylamino-but-2-yl, 8-aza-bicyclo[3.2.1]octanyl, 1-aza-bicyclo[2.2.2]octanyl, and 2-(methylamino)-ethyl;

wherein pyrrolidin-2-yl of pyrrolidin-2-ylmethyl is optionally substituted at a nitrogen atom with methyl;

and enantiomers, diastereomers, solvates, and pharmaceutically acceptable salts thereof.

Another aspect of the present invention is directed to a compound of Formula (I)

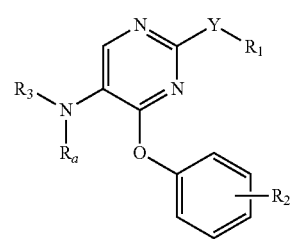

Formula (I)

wherein

R₁ is phenyl optionally substituted with one to two substituents independently selected from the group consisting of $C_{1-4}$alkoxy and fluoro; in addition, $R_1$ is optionally substituted with di($C_{1-4}$alkyl)aminocarbonyl;

Y is O or ethynyl;

$R_2$ is a substituent selected from the group consisting of $C_{1-2}$alkoxy, fluoro, and bromo;

$R_a$ is hydrogen;

$R_3$ is selected from the group consisting of pyrrolidin-2-ylmethyl, piperidin-3-yl, and 3-amino-cyclohexyl;

wherein pyrrolidin-2-yl of pyrrolidin-2-ylmethyl is optionally substituted at a nitrogen atom with methyl;

and enantiomers, diastereomers, solvates, and pharmaceutically acceptable salts thereof.

Another embodiment of the present invention is directed to a compound of Formula (I)

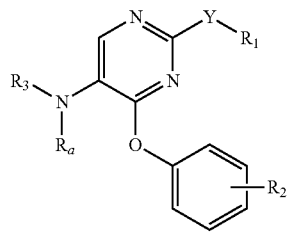

Formula (I)

wherein $R_1$ is phenyl optionally substituted with one substituent independently selected from the group consisting of $C_{1-4}$alkoxy and di($C_{1-4}$alkyl)aminocarbonyl;

Y is O;

$R_2$ is $C_{1-2}$alkoxy or fluoro;

$R_a$ is hydrogen;

$R_3$ is selected from the group consisting of pyrrolidin-2-ylmethyl, piperidin-3-yl, and 3-amino-cyclohexyl;

wherein pyrrolidin-2-yl of pyrrolidin-2-ylmethyl is optionally substituted at a nitrogen atom with methyl;

and enantiomers, diastereomers, solvates, and pharmaceutically acceptable salts thereof.

Compounds of Formula (I) include compounds of Formula (II)

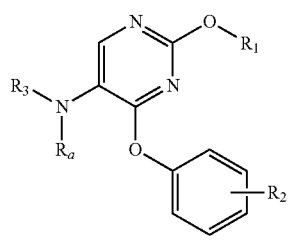

Formula (II)

wherein $R_1$, $R_2$, $R_a$, and $R_3$ are as defined herein; and enantiomers, diastereomers, solvates, and pharmaceutically acceptable salts thereof.

A further embodiment of the present invention is directed to a compound of Formula (I)

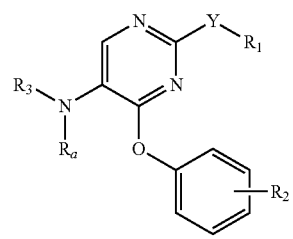

Formula (I)

selected from the group consisting of:
a compound of Formula (I) wherein $R_1$ is 4-methoxy-phenyl, Y is O, $R_2$ is 4-methoxy, $R_a$ is H, and $R_3$ is pyrrolidin-2-ylmethyl; (2S)
a compound of Formula (I) wherein $R_1$ is 4-methoxy-phenyl, Y is O, $R_2$ is 4-methoxy, $R_a$ is H, and $R_3$ is piperidin-3-yl; (RS)
a compound of Formula (I) wherein $R_1$ is 4-methoxy-phenyl, Y is O, $R_2$ is 4-methoxy, $R_a$ is H, and $R_3$ is 3-amino-cyclohexyl; (1RS,3RS)
a compound of Formula (I) wherein $R_1$ is 2-phenyl, Y is ethynyl, $R_2$ is 4-methoxy, $R_a$ is H, and $R_3$ is pyrrolidin-2-ylmethyl; (2S)
a compound of Formula (I) wherein $R_1$ is 4-diethylaminocarbonyl-phenyl, Y is O, $R_2$ is 4-methoxy, $R_a$ is H, and $R_3$ is pyrrolidin-2-ylmethyl; (2S)
a compound of Formula (I) wherein $R_1$ is 4-methoxy-phenyl, Y is O, $R_2$ is 4-methoxy, $R_a$ is H, and $R_3$ is pyrrolidin-2-ylmethyl; (2RS)
a compound of Formula (I) wherein $R_1$ is 4-methoxy-phenyl, Y is O, $R_2$ is 4-methoxy, $R_a$ is H, and $R_3$ is pyrrolidin-2-ylmethyl; (2R)
a compound of Formula (I) wherein $R_1$ is 4-methoxy-phenyl, Y is O, $R_2$ is 4-methoxy, $R_a$ is methyl, and $R_3$ is 1-methyl-pyrrolidin-2-ylmethyl; (2S)
a compound of Formula (I) wherein $R_1$ is 4-methoxy-phenyl, Y is O, $R_2$ is 4-methoxy, $R_a$ is H, and $R_3$ is 1-methyl-pyrrolidin-2-ylmethyl; (2S)
a compound of Formula (I) wherein $R_1$ is 4-methoxy-phenyl, Y is O, $R_2$ is 4-methoxy, $R_a$ is H, and $R_3$ is 3-hydroxy-2-amino-propyl; (2R)
a compound of Formula (I) wherein $R_1$ is 4-methoxy-phenyl, Y is O, $R_2$ is 4-methoxy, $R_a$ is H, and $R_3$ is 8-aza-bicyclo[3.2.1]oct-3-yl; (1R,5S)
a compound of Formula (I) wherein $R_1$ is 4-methoxy-phenyl, Y is O, $R_2$ is 4-methoxy, $R_a$ is H, and $R_3$ is piperidin-4-yl;
a compound of Formula (I) wherein $R_1$ is 4-methoxy-phenyl, Y is O, $R_2$ is 4-methoxy, $R_a$ is H, and $R_3$ is azetidin-3-ylmethyl;
a compound of Formula (I) wherein $R_1$ is 4-methoxy-phenyl, Y is O, $R_2$ is 4-methoxy, $R_a$ is H, and $R_3$ is 1-aza-bicyclo[2.2.2]oct-3-yl;
a compound of Formula (I) wherein $R_1$ is 4-methoxy-phenyl, Y is O, $R_2$ is 4-methoxy, $R_a$ is H, and $R_3$ is piperidin-3-ylmethyl; (3RS)
a compound of Formula (I) wherein $R_1$ is 4-methoxy-phenyl, Y is O, $R_2$ is 4-methoxy, $R_a$ is H, and $R_3$ is 4-amino-cyclohexyl;
a compound of Formula (I) wherein $R_1$ is 4-methoxy-phenyl, Y is O, $R_2$ is 4-methoxy, $R_a$ is H, and $R_3$ is piperidin-4-ylmethyl;
a compound of Formula (I) wherein $R_1$ is 4-methoxy-phenyl, Y is O, $R_2$ is 4-methoxy, $R_a$ is H, and $R_3$ is 2-methylamino-ethyl;

a compound of Formula (I) wherein $R_1$ is 2-(4-methoxyphenyl), Y is vinyl, $R_2$ is 4-methoxy, $R_a$ is H, and $R_3$ is pyrrolidin-2-ylmethyl; (2S)

a compound of Formula (I) wherein $R_1$ is 4-methoxy-phenyl, Y is S(O), $R_2$ is 4-methoxy, $R_a$ is H, and $R_3$ is pyrrolidin-2-ylmethyl; (2S)

a compound of Formula (I) wherein $R_1$ is 4-methoxy-phenyl, Y is O, $R_2$ is 4-methoxy, $R_a$ is H, and $R_3$ is 3-hydroxy-2-amino-propyl; (2S)

a compound of Formula (I) wherein $R_1$ is 4-methoxy-phenyl, Y is O, $R_2$ is 4-methoxy, $R_a$ is H, and $R_3$ is pyrrolidin-3-ylmethyl; (3RS)

a compound of Formula (I) wherein $R_1$ is 4-methoxy-phenyl, Y is NH, $R_2$ is 4-methoxy, $R_a$ is H, and $R_3$ is pyrrolidin-2-ylmethyl; (2S)

a compound of Formula (I) wherein $R_1$ is 4-fluoro-phenyl, Y is O, $R_2$ is 4-fluoro, $R_a$ is H, and $R_3$ is pyrrolidin-2-ylmethyl; (2*S)

a compound of Formula (I) wherein $R_1$ is 4-methoxy-phenyl, Y is O, $R_2$ is 4-methoxy, $R_a$ is H, and $R_3$ is piperidin-2-ylmethyl; (2RS)

a compound of Formula (I) wherein $R_1$ is 2-bromo-phenyl, Y is O, $R_2$ is 2-bromo, $R_a$ is H, and $R_3$ is pyrrolidin-2-ylmethyl; (2S)

a compound of Formula (I) wherein $R_1$ is 4-methoxy-phenyl, Y is O, $R_2$ is 4-methoxy, $R_a$ is H, and $R_3$ is 1-phenylmethyl-pyrrolidin-3-yl; (3RS)

a compound of Formula (I) wherein $R_1$ is 4-methoxy-phenyl, Y is O, $R_2$ is 4-methoxy, $R_a$ is H, and $R_3$ is 1-phenylmethyl-piperidin-4-yl;

a compound of Formula (I) wherein $R_1$ is 4-methoxy-phenyl, Y is O, $R_2$ is 4-methoxy, $R_a$ is H, and $R_3$ is 1-phenethyl-piperidin-4-yl;

a compound of Formula (I) wherein $R_1$ is 4-methoxy-phenyl, Y is O, $R_2$ is 4-methoxy, $R_a$ is H, and $R_3$ is 1-methyl-piperidin-4-yl;

a compound of Formula (I) wherein $R_1$ is 4-methoxy-phenyl, Y is O, $R_2$ is 4-methoxy, $R_a$ is H, and $R_3$ is morpholin-2-ylmethyl; (2RS) a compound of Formula (I) wherein $R_1$ is 4-methoxy-phenyl, Y is O, $R_2$ is 4-methoxy, $R_a$ is H, and $R_3$ is 1-phenylmethyl-piperidin-3-yl; (3RS) a compound of Formula (I) wherein $R_1$ is 4-methoxy-phenyl, Y is O, $R_2$ is 4-methoxy, $R_a$ is H, and $R_3$ is 2-(piperidin-4-yl)-ethyl;

a compound of Formula (I) wherein $R_1$ is 4-methoxy-phenyl, Y is O, $R_2$ is 4-methoxy, $R_a$ is H, and $R_3$ is 2-(piperidin-3-yl)-ethyl; (3RS)

a compound of Formula (I) wherein $R_1$ is 4-methoxy-phenyl, Y is O, $R_2$ is 4-methoxy, $R_a$ is H, and $R_3$ is 4-phenyl-piperidin-3-yl; (3RS, 4RS)

a compound of Formula (I) wherein $R_1$ is 4-methoxy-phenyl, Y is O, $R_2$ is 4-methoxy, $R_a$ is H, and $R_3$ is pyrrolidin-3-yl; (3RS)

a compound of Formula (I) wherein $R_1$ is 4-methoxy-phenyl, Y is O, $R_2$ is 4-methoxy, $R_a$ is H, and $R_3$ is 4-(imidazol-1-yl)-phenylmethyl;

a compound of Formula (I) wherein $R_1$ is 4-methoxy-phenyl, Y is O, $R_2$ is 4-methoxy, $R_a$ is H, and $R_3$ is 4-diethylamino-but-2-yl; (2RS)

a compound of Formula (I) wherein $R_1$ is 4-methoxy-phenyl, Y is O, $R_2$ is 4-methoxy, $R_a$ is H, and $R_3$ is pyridin-4-ylmethyl;

a compound of Formula (I) wherein $R_1$ is 4-methoxy-phenyl, Y is O, $R_2$ is 4-methoxy, $R_a$ is H, and $R_3$ is 1-(pyridin-4-yl)-ethyl; (IRS)

a compound of Formula (I) wherein $R_1$ is 4-methoxy-phenyl, Y is O, $R_2$ is 4-methoxy, $R_a$ is H, and $R_3$ is 1-methylcarbonyl-piperidin-4-yl;

a compound of Formula (I) wherein $R_1$ is 4-methoxy-phenyl, Y is O, $R_2$ is 4-methoxy, $R_a$ is H, and $R_3$ is 1H-imidazol-2-ylmethyl;

a compound of Formula (I) wherein $R_1$ is 4-methoxy-phenyl, Y is O, $R_2$ is 4-methoxy, $R_a$ is H, and $R_3$ is thiazol-2-ylmethyl;

a compound of Formula (I) wherein $R_1$ is 4-methoxy-phenyl, Y is O, $R_2$ is 4-methoxy, $R_a$ is H, and $R_3$ is 2-guanidino-ethyl;

a compound of Formula (I) wherein $R_1$ is pyridin-3-yl, Y is O, $R_2$ is 4-methoxy, $R_a$ is H, and $R_3$ is pyrrolidin-2-ylmethyl; (2S)

a compound of Formula (I) wherein $R_1$ is 3-fluoro-phenyl, Y is O, $R_2$ is 4-methoxy, $R_a$ is H, and $R_3$ is pyrrolidin-2-ylmethyl; (2S)

a compound of Formula (I) wherein $R_1$ is 3-fluoro-phenyl, Y is S, $R_2$ is 4-methoxy, $R_a$ is H, and $R_3$ is pyrrolidin-2-ylmethyl; (2S)

a compound of Formula (I) wherein $R_1$ is pyridin-3-yl, Y is NH, $R_2$ is 4-methoxy, $R_a$ is H, and $R_3$ is pyrrolidin-2-ylmethyl; (2S)

a compound of Formula (I) wherein $R_1$ is 3-fluoro-phenyl, Y is NH, $R_2$ is 4-methoxy, $R_a$ is H, and $R_3$ is pyrrolidin-2-ylmethyl; (2S)

a compound of Formula (I) wherein $R_1$ is thiazol-2-yl, Y is NH, $R_2$ is 4-methoxy, $R_a$ is H, and $R_3$ is pyrrolidin-2-ylmethyl; (2S)

a compound of Formula (I) wherein $R_1$ is 3-chloro-phenyl, Y is O, $R_2$ is 4-methoxy, $R_a$ is H, and $R_3$ is pyrrolidin-2-ylmethyl; (2S)

a compound of Formula (I) wherein $R_1$ is 3-methoxy-phenyl, Y is O, $R_2$ is 4-methoxy, $R_a$ is H, and $R_3$ is pyrrolidin-2-ylmethyl; (2S)

a compound of Formula (I) wherein $R_1$ is 3-cyano-phenyl, Y is O, $R_2$ is 4-methoxy, $R_a$ is H, and $R_3$ is pyrrolidin-2-ylmethyl; (2S) and a compound of Formula (I) wherein $R_1$ is 3,5-difluoro-phenyl, Y is O, $R_2$ is 4-methoxy, $R_a$ is H, and $R_3$ is pyrrolidin-2-ylmethyl; (2S)

and pharmaceutically acceptable salts thereof.

For use in medicine, salts of compounds of formula (I) refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, where the compounds of formula (I) carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid;

and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of formula (I). In general, such prodrugs will be functional derivatives of the compounds that are readily convertible in vivo into the required compound. Thus, in the methods of treatment of embodiments of the present invention, the term "administering" encompasses the treatment of the various disorders described with the compound specifically disclosed or with a compound which may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition comprising the (+)-1-enantiomer of a compound of formula (I) wherein said composition is substantially free from the (−)-isomer of said compound. In the present context, substantially free means less than 25%, preferably less than 10%, more preferably less than 5%, even more preferably less than 2% and even more preferably less than 1% of the (−)-isomer calculated as.

$$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100$$

Another embodiment of the present invention is a composition comprising the (−)-enantiomer of a compound of formula (I) wherein said composition is substantially free from the (+)-isomer of said compound. In the present context, substantially free from means less than 25%, preferably less than 10%, more preferably less than 5%, even more preferably less than 2% and even more preferably less than 1% of the (+)-isomer calculated as $$\%(-) - \text{enantiomer} = \frac{(\text{mass}(-) - \text{enantiomer})}{(\text{mass}(+) - \text{enantiomer}) + (\text{mass}(-) - \text{enantiomer})} \times 100.$$

During any of the processes for preparation of the compounds of embodiments of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice. Thus, particular embodiments of the present invention are directed to pharmaceutical compositions comprising compounds of formula (I) and one or more than one pharmaceutically acceptable carrier, excipient or diluent.

By way of example, in the pharmaceutical and veterinary compositions of embodiments of the present invention, the compounds of formula (I) may be admixed with any suitable binder(s), lubricant(s), suspending agent(s), coating agent(s), and/or solubilizing agent(s).

Tablets or capsules of the compounds may be administered one or two or more at a time, as appropriate. It is also possible to administer the compounds in sustained release formulations.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin. They can also be incorporated, at a concentration of between 1% and 10% by weight, into an ointment consisting of a white wax or white soft paraffin base together with such stabilizers and preservatives as may be required. An alternative means of transdermal administration is by use of a skin patch.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly, subcutaneously, intradermally or intrathecally. In this case, the compositions will comprise a suitable carrier or diluent.

For parenteral administration, the compositions are best used in the form of a sterile aqueous solution which may contain other substances, for example, enough salts or monosaccharides to make the solution isotonic with blood.

For buccal or sublingual administration, the compositions may be administered in the form of tablets or lozenges, which can be formulated in a conventional manner.

By way of further example, pharmaceutical and veterinary compositions containing one or more of the compounds of formula (I) as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral, etc.). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations also may be coated with substances such as sugars or be enterically-coated so as to modulate the major site of absorption. For parenteral administration, the carrier will usually consist of sterile water, and other ingredients may be added to increase solubility or preservation. Injectable suspensions or solutions may also be prepared utilizing aqueous carriers along with appropriate additives.

A therapeutically effective amount of compounds of formula (I) or a pharmaceutical composition thereof comprises a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Advantageously, compounds of formula (I) may be administered in a single daily dose, or the total daily dosage may be administered in divided doses of two, three or four times daily. Furthermore, compounds of formula (I) can be administered in intranasal form via topical use of suitable intranasal vehicles, or via transdermal skin patches well known to those skilled in that art.

It is also apparent to one skilled in the art that the therapeutically effective dose for active compounds of formula (I) or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of the compounds of formula (I) as analgesics is required for a subject in need thereof.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulitis, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the diseases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:
AcCl acetyl chloride
AcOH glacial acetic acid
aq. aqueous
Bn or Bzl benzyl
conc. Concentrated
dba dibenzylideneacetone
DBU 1,8-diazabicyclo[5.4.0]undec-7-ene
DCE dichloroethane
DCM dichloromethane
DIEA diisopropylethylamine
DMF N,N-dimethylformamide
DMSO dimethylsulfoxide
dppf 1,1'-bis(diphenylphosphino)ferrocene
ESI electron-spray ionization
EtOAc ethyl acetate
EtOH ethanol
h or hrs hour(s)
HATU O-(1H-7-azabenzotriazol-1-yl)-1,1,3,3-tetramethyl-uronium-hexafluorophosphate
HOBt 1-hydroxybenzotriazole
HPLC high performance liquid chromatography
Me methyl
MeOH methanol
MHz megahertz
min minutes
MPLC medium pressure liquid chromatography
MS mass spectrometry
NMR nuclear magnetic resonance
Ph phenyl
Pd/C palladium on activated carbon
Ph$_3$P triphenylphosphine
PyBOP (Benzotriazol-1-yloxy)-tripyrrolidinophosphonium-hexafluorophosphate
rt room temperature
TEA/Et$_3$N triethylamine
TFA trifluoroacetic acid
THF tetrahydrofuran
TLC thin layer chromatography
TMS tetramethylsilane Scheme A illustrates a route for the synthesis of compounds of Formula (I)-A wherein R$_1$ is optionally substituted phenyl, Y is O, S, or NH, and R$_3$ is piperidinyl, amino-C$_{3-6}$cycloalkyl, or pyrrolidinyl.

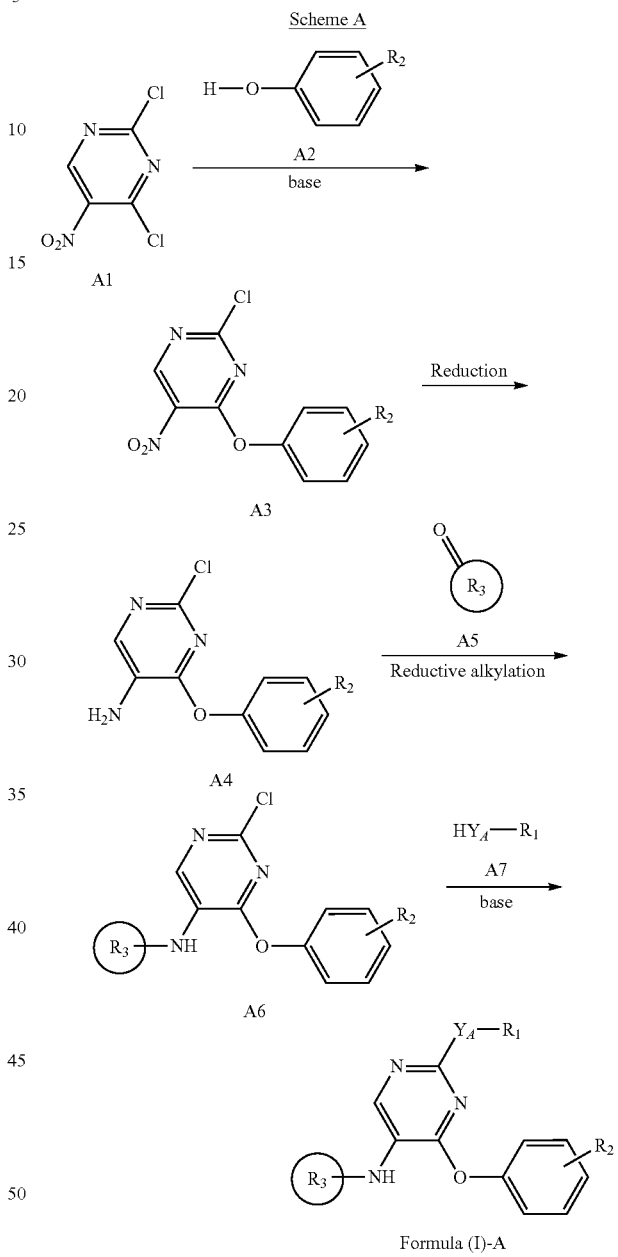

Scheme A

The compound of formula A1 is either commercially available or can be made by known methods described in the scientific literature. A compound of formula A1 may be treated with a compound of formula A2 under basic conditions to afford a compound of formula A3. The nitro group of a compound of formula A3 may be reduced to its corresponding primary amino group of formula A4 by the action of a reducing agent such as zinc, tin, or iron in acetic acid, or by catalytic hydrogenation. The resultant amino group of a compound of formula A4 may undergo a reductive alkylation with a ketone of formula A5 (wherein ring R$_3$ is piperidinyl, amino substituted-C$_{3-6}$cycloalkyl, or pyrrolidinyl) in the presence of a hydride source such as triacetoxysodium borohydride to afford a compound of formula A6. Ketones of formula A5 wherein ring R$_3$ is a heterocycle may require conventional removal of an amino protecting group following the reductive alkylation step. For example, Boc-protected amines may be deprotected under acidic conditions using reagents such as HCl, TFA, and the like. Likewise, Cbz-protected amines may be deprotected under acidic conditions.

A compound of formula A6 may be treated with an $R_1$-substituted nucleophile of the formula A7 (wherein $Y_A$ is O, S, or NH) under basic conditions to afford a compound of formula (I)-A.

Scheme B illustrates a route for the synthesis of compounds of Formula (I)-B wherein $R_1$ is optionally substituted phenyl, Y is O, S, or NH, and $R_3$ is selected from the group consisting of pyrrolidinylmethyl, piperidinylethyl, pyridin-4-yl-$C_{1-2}$alkyl, azetidin-3-ylmethyl, morpholinylmethyl, imidazolylmethyl, thiazolylmethyl, 4-(imidazol-1-yl)phenylmethyl, 2-(methylamino)-ethyl, and 2-diethylamino-ethyl.

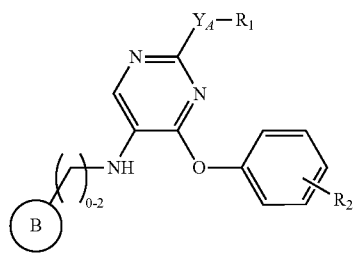

Formula (I)-B

A compound of formula A4 may undergo a reductive alkylation with an aldehyde of formula B1 in the presence of a hydride source such as triacetoxysodium borohydride to afford compounds of formula B1 of the present invention. Ring B of the compounds of formula B1 is selected from the group consisting of pyrrolidinyl, piperidinyl, pyridinyl, azetidinyl, morpholinyl, imidazolyl, thiazolyl, and 4-(imidazol-1-yl)-phenyl). Aldehydes of formula B1 wherein ring B is nitrogen-containing and saturated may require conventional removal of an amino protecting group following the reductive alkylation step. A compound of formula B1 may be treated with an $R_1$-substituted nucleophile of the formula A7 under basic conditions to afford a compound of formula (I)-B.

Scheme C illustrates a route for the synthesis of compounds of Formula (I)-C1, Formula (I)-C2 wherein $R_a$ is methyl, and Formula (I)-C3; wherein $R_3$ is a pyrrolidinyl or piperidinyl-containing substituent wherein pyrrolidinyl and piperidinyl are optionally substituted at a nitrogen atom with methyl, phenylmethyl, or phenethyl.

Scheme B

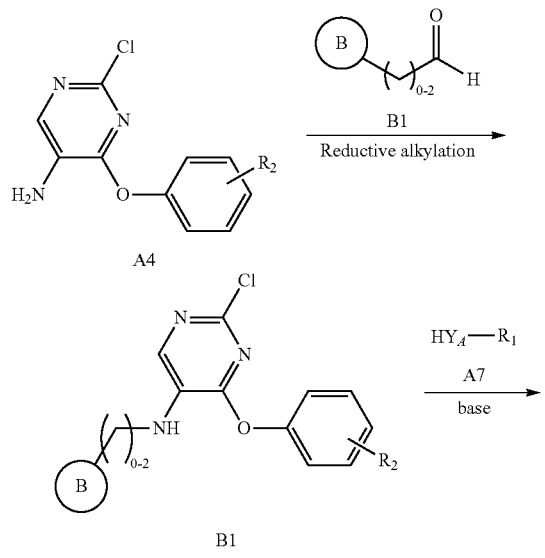

Scheme C

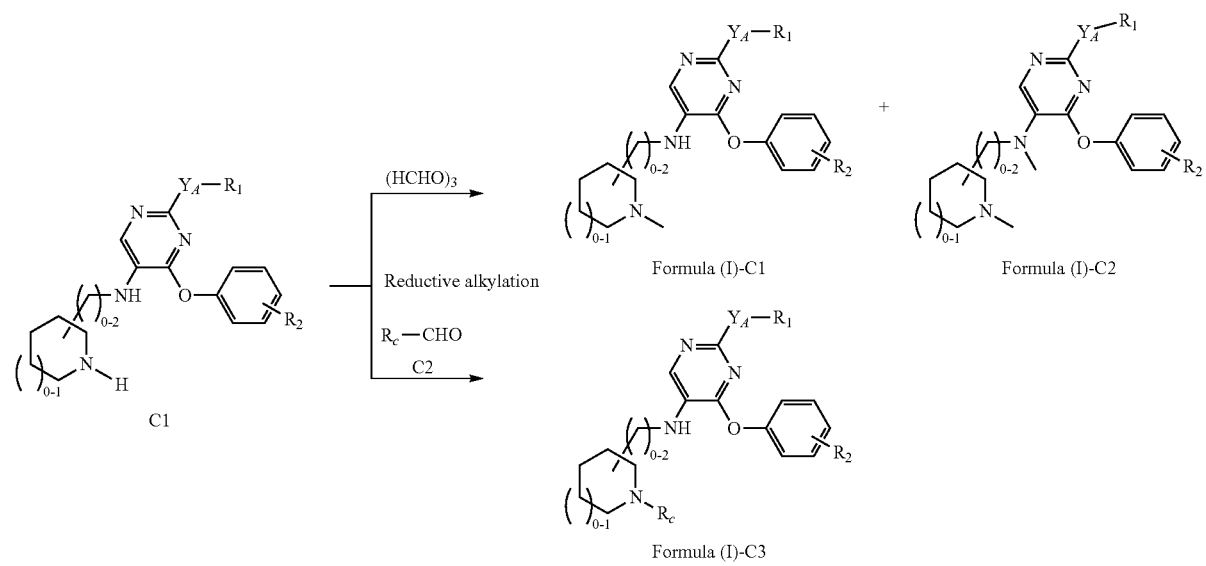

A compound of formula C1, prepared as described generically in Scheme B, may undergo a reductive alkylation with formalin under acidic conditions and in the presence of a hydride source such as NaBH$_3$CN to afford mono-methylated compounds of formula (I)-C1 and dimethylated compounds of formula (I)-C2 of the present invention. Similarly, a compound of formula C1 may undergo a reductive alkylation with an appropriately substituted aldehyde (C2), wherein R$_c$ is phenyl or benzyl, in the presence of a hydride source, to form compounds of formula (I)-C3 wherein R$_c$ is phenylmethyl or phenethyl, respectively.

Scheme D illustrates a route for the synthesis of compounds of Formula (I)-D wherein Y is O, S, or NH and R$_3$ is 3-hydroxy-2-amino-propyl.

Scheme E illustrates a route for the synthesis of compounds of Formula (I)-E wherein R$_3$ is guanidinyl-ethyl.

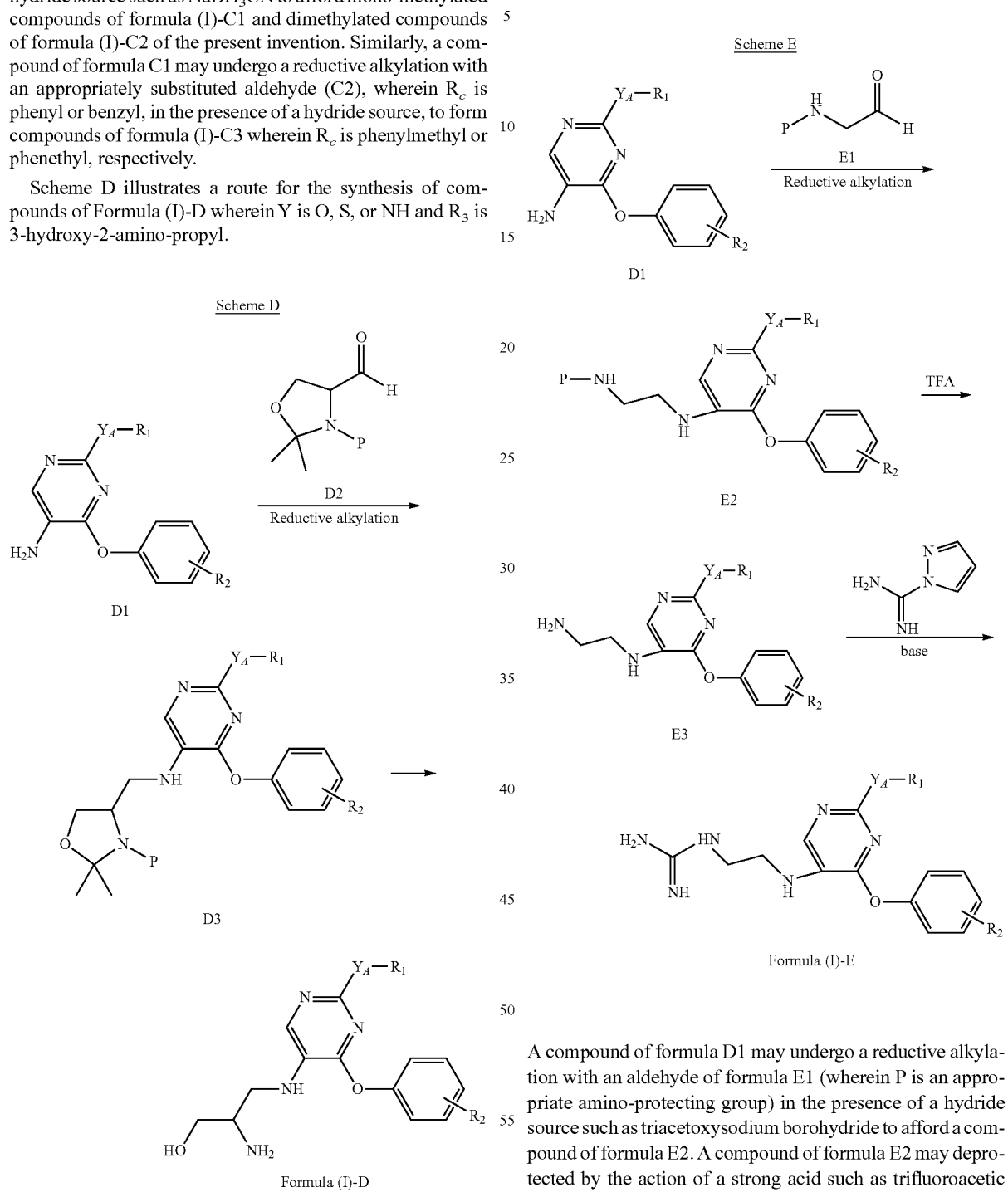

A compound of formula D1 may undergo a reductive alkylation with an aldehyde of formula D2 (wherein P is an appropriate amino-protecting group) in the presence of a hydride source such as triacetoxysodium borohydride to afford a compound of formula D3. A compound of formula D3 may deprotected by the action of a strong acid such as trifluoroacetic acid to afford a compound of formula (I)-D.

A compound of formula D1 may undergo a reductive alkylation with an aldehyde of formula E1 (wherein P is an appropriate amino-protecting group) in the presence of a hydride source such as triacetoxysodium borohydride to afford a compound of formula E2. A compound of formula E2 may deprotected by the action of a strong acid such as trifluoroacetic acid to afford a compound of formula E3, and the primary amine subsequently may be treated with 1H-pyrazole-1-carboxamidine hydrochloride in the presence of a tertiary amine to afford a guanidinyl-substituted compound of formula (I)-E.

Scheme F illustrates a route for the synthesis of compounds of Formula (I)-F1 and Formula (I)-F2 wherein Y is S or S(O), respectively.

Scheme F

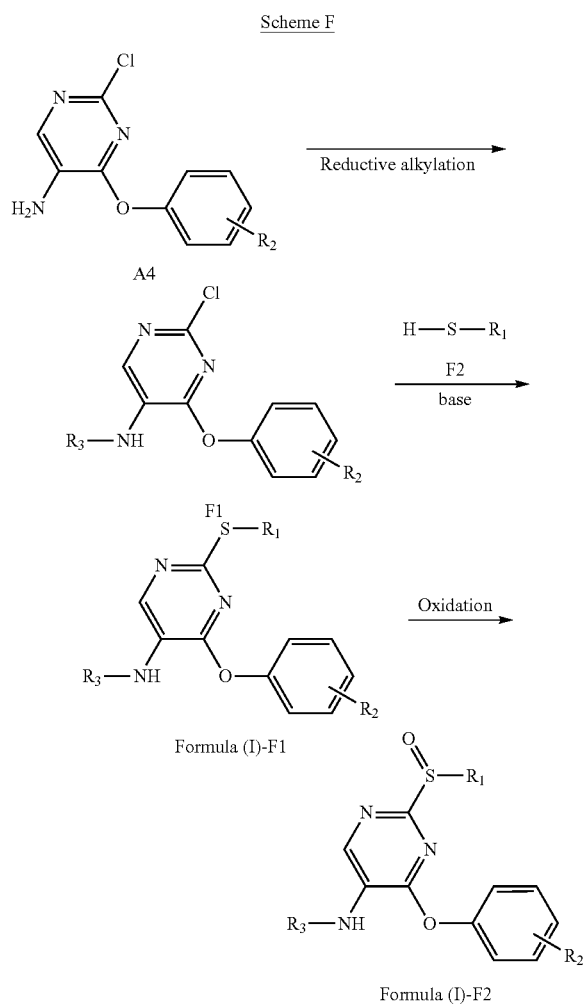

The amino group of a compound of formula A4 may undergo a reductive alkylation with an appropriately substituted ketone or aldehyde as defined herein to afford an $R_3$-substituted compound of formula F1. A compound of formula F1 may participate in an aromatic nucleophilic replacement with a compound of formula F2 to afford a compound of Formula (I)-F1 wherein Y is S. Subsequent exposure to air slowly converted a compound of formula (I)-F1 to a corresponding compound of formula (I)-F2 wherein Y is S(O).

Scheme G illustrates a route for the synthesis of compounds of Formula (I)-G wherein Y is vinyl.

Scheme G

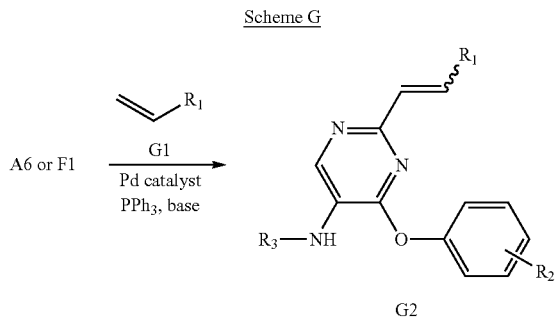

A compound of formula G1 is either commercially available or may be prepared by known methods described in the literature. The chloride of formula A6 or F1 may be cross-coupled with a compound of formula G1 in the presence of a palladium catalyst, appropriate ligands, and an inorganic base to afford a compound of formula (I)-G.

Scheme H illustrates a route for the synthesis of compounds of Formula (I)-H wherein Y is NH.

Scheme H

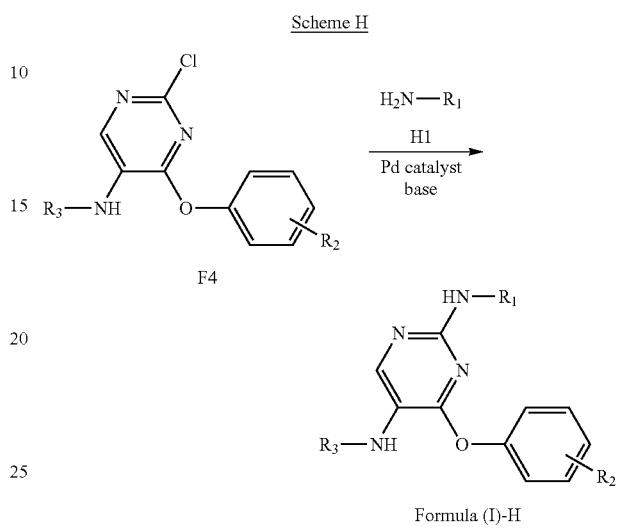

A compound of formula H1 is either commercially available or may be prepared by known methods described in the literature. A compound of formula F4 may be treated with a compound of formula H1 in the presence of a palladium catalyst, phosphine ligands, and an inorganic base to afford a compound of formula (I)-H.

Scheme I illustrates a route for the synthesis of compounds of Formula (I)-I wherein Y is ethynyl.

Scheme I

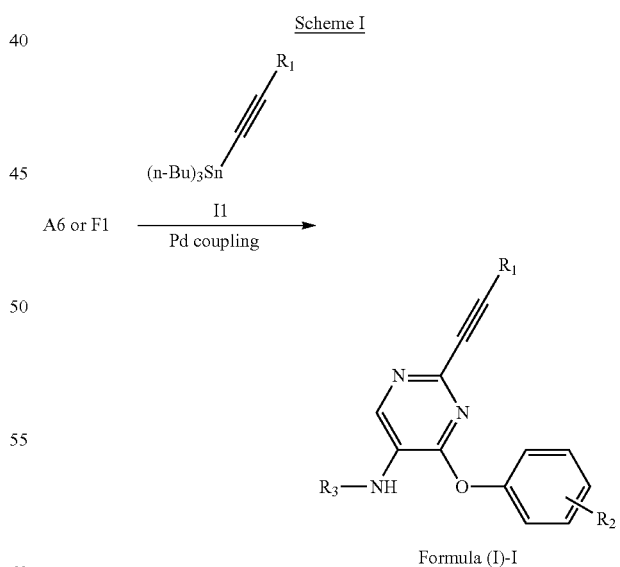

Compounds of formula I1 are either commercially available or readily prepared according to chemistry found in the literature. An aryl chloride of formula A6 or F1 may be cross-coupled with a tin reagent of formula I1 in the presence of a palladium catalyst such as tetrakis(triphenylphosphine)palladium (0) to afford a compound of formula (I)-I.

Scheme J illustrates a route for the synthesis of compounds of Formula (I)-J wherein R₃ is a pyrrolidinyl or piperidinyl-containing substituent wherein pyrrolidinyl and piperidinyl are optionally substituted at a nitrogen atom with methylcarbonyl.

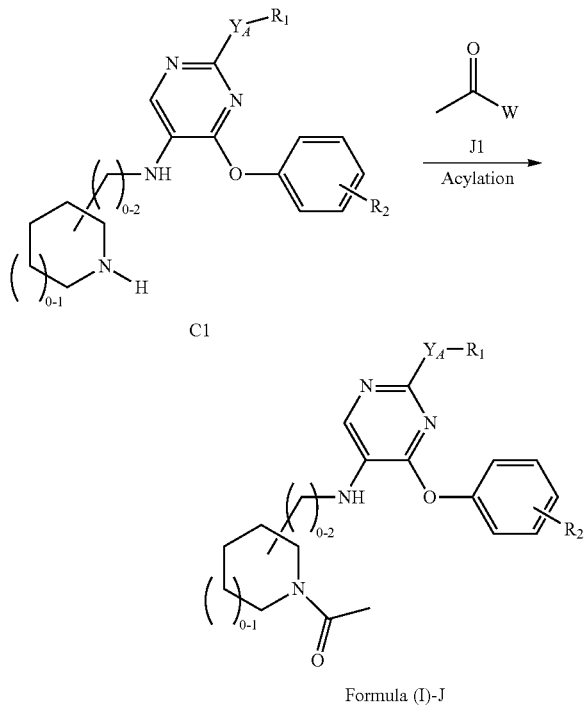

Formula (I)-J

A compound of formula C1 may be acylated with a compound of formula J1 wherein W is chloro, acetoxy, or an activated alkoxide to form a compound of formula (I)-J.

Scheme K illustrates a route for the synthesis of compounds of Formula (I)-K wherein R₁ is optionally substituted phenyl and bears substituents that differ from R₂; and Y_A is O, S, or NH, and R₃ is piperidinyl, amino-C₃₋₆cycloalkyl, or pyrrolidinyl.

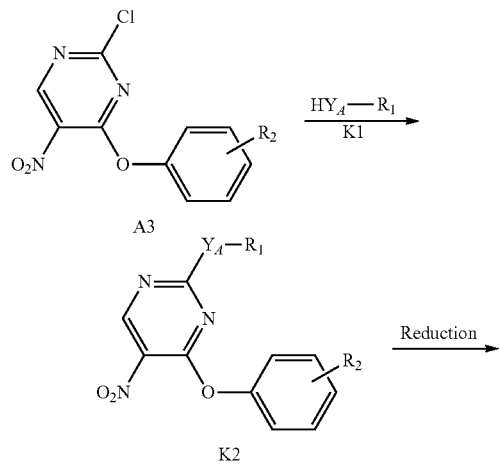

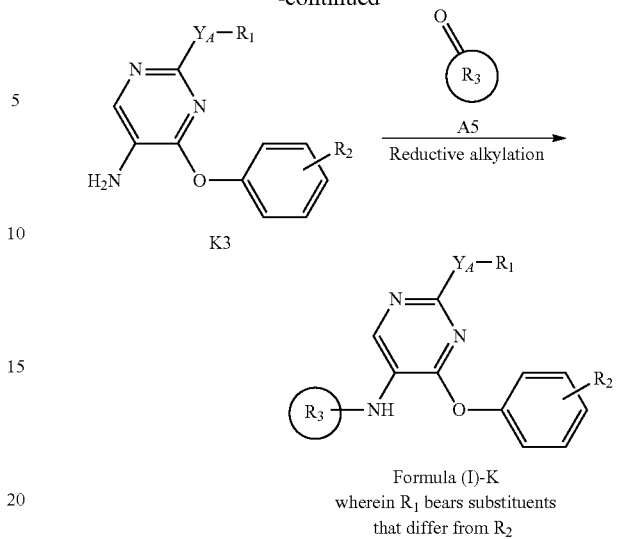

Formula (I)-K
wherein R₁ bears substituents
that differ from R₂

A compound of formula A3 may undergo an aromatic nucleophilic displacement with a compound of formula K1, wherein Y_A is O, S, or NH and R₁ is as defined herein. Reduction of the nitro group followed by reductive alkylation with a compound of formula A5 affords a compound of formula (I)-K.

Specific Examples

Reagents were purchased from commercial sources. Nuclear magnetic resonance (NMR) spectra for hydrogen atoms were measured in the indicated solvent with (TMS) as the internal standard on a Bruker Avance or Varian (300 or 400 MHz) spectrometer. The values are expressed in parts per million downfield from TMS. The mass spectra (MS) were determined on a Micromass Platform LC or Agilent 1100 LCMS spectrometer as (ESI) m/z (M+H⁺) using an electrospray technique. Microwave accelerated reactions were performed using a CEM Discover or Biotage microwave instrument, and were contained in a sealed pressure vessel unless otherwise noted. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

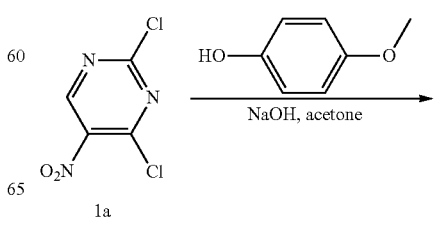

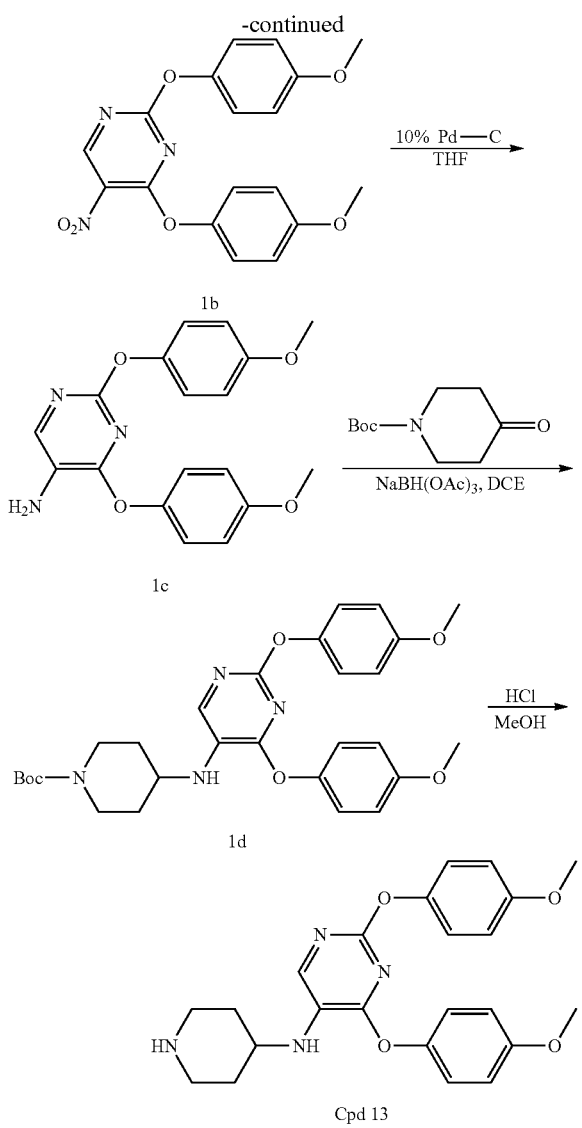

C. 4-[2,4-Bis-(4-methoxyphenoxy)pyrimidin-5-ylamino]piperidine-1-carboxylic acid tert-butyl ester (1d) To a solution of Compound 1c (1.12 g; 3.3 mmol) and tert-butyl 4-oxo-1-piperidinecarboxylate (0.67 g; 3.3 mmol) in DCE (17 mL) was added NaBH(OAc)$_3$ (1.05 g; 4.95 mmol). The resulting mixture was stirred under a nitrogen atmosphere at room temperature for 22 h. Aqueous work-up and purification by flash column chromatography (eluent, EtOAc/hexanes:3/7) gave Compound 1d (1.06 g; 61%). $^1$H-NMR (300 MHz, CDCl$_3$): δ 7.66 (s, 1H), 7.08-7.11 (d, 2H), 7.00-7.03 (d, 2H), 6.89-6.92 (d, 2H), 6.83-6.86 (d, 2H), 4.04-4.08 (m, 2H), 3.81 (s, 3H), 3.78 (s, 3H), 3.36-3.38 (m, 1H), 2.90-2.98 (m, 2H), 2.04-2.09 (m, 2H), 1.46 (s, 9H), 1.40-1.47 (m, 2H); MS: m/z 523.3 (M+H)$^+$.

D. 2,4-Bis-(4-methoxyphenoxy)pyrimidin-5-yl]piperidin-4-ylamine (Cpd 13) To a solution of Compound 1d (0.08 g; 0.15 mmol) in MeOH (1 mL) was added 4N HCl in dioxane (2 mL). The mixture was stirred at 50° C. for 1 h and evaporated to dryness. The residue was washed with Et$_2$O twice and dried to give Compound 13 as a HCl salt in a quantitative yield. $^1$H-NMR (300 MHz, CD$_3$OD): δ 7.94 (s, 1H), 7.01-7.04 (d, 2H), 6.96-6.99 (d, 2H), 6.83-6.86 (d, 2H), 6.80-6.83 (d, 2H), 3.78 (s, 1H), 3.77 (s, 1H), 3.70-3.73 (m, 1H), 3.48-3.52 (m, 2H), 3.14-3.23 (m, 2H), 2.28-2.32 (m, 2H), 1.81-1.85 (m, 2H); MS: m/z 423.3 (M+H)$^+$.

Following the procedure described above for Example 1 and substituting the appropriate reagents, starting materials and purification methods known to those skilled in the art, the following compounds of the present invention were prepared:

| Cpd | MS (M + H)$^+$ | Cpd | MS (M + H)$^+$ |
| --- | --- | --- | --- |
| 2 | 423.2 | 3 | 437.2 |
| 12 | 449.2 | 17 | 437.2 |
| 36 | 499.2 | 37 | 409.2 |

Example 2

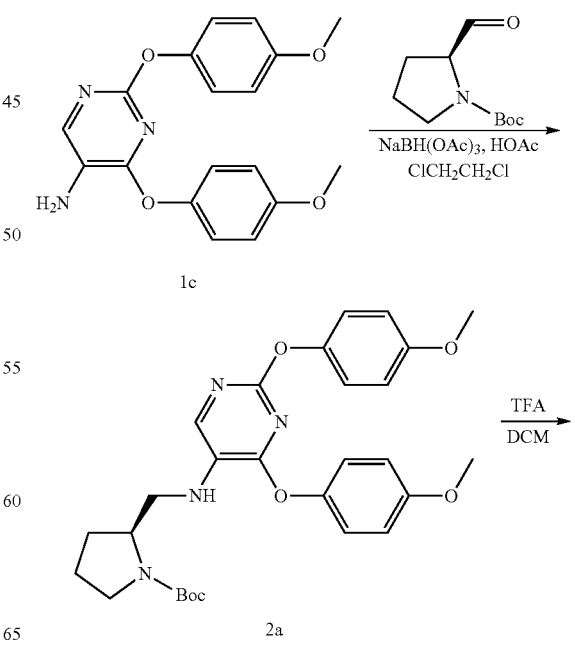

A. 2,4-Bis-(4-methoxyphenoxy)-5-nitropyrimidine (1b) To a solution of 2,4-dichloro-5-nitropyrimidine (Compound 1a) (0.5 g; 2.6 mmol) in acetone (40 mL) was added a solution of 4-methoxyphenol (0.71 g; 5.7 mmol) in 1N NaOH aqueous solution (5.7 mL; 5.7 mmol) and H$_2$O (20 mL) dropwise. After completion of addition, the reaction mixture was allowed to warm to room temperature slowly and stirred at room temperature for 20 h. Upon removal of solvents by evaporation, the residue was extracted with EtOAc, washed sequentially with 1N NaOH$_{(aq)}$ and brine, and dried over MgSO$_4$. The mixture was filtered, concentrated, and purified by flash column chromatography (eluent, EtOAc/hexanes:1/4 to 1/1) to afford Compound 1b as a yellow solid (1.0; 100%). $^1$H-NMR (300 MHz, CDCl$_3$): δ 9.16 (s, 1H), 7.03-7.07 (d, 2H), 6.95-6.98 (d, 2H), 6.86-6.89 (d, 2H), 6.82-6.85 (d, 2H), 3.82 (s, 1H), 3.80 (s, 1H); MS: m/z 370.2 (M+H)$^+$.

B. 2,4-Bis-(4-methoxy-phenoxy)-pyrimidin-5-ylamine (1c) To a solution of Compound 1b (1.25 g; 3.38 mmol) in THF (30 mL) was added 10% Pd—C (0.5 g) and the mixture was shaken under a 50 psi hydrogen atmosphere in a Parr hydrogenator for 17 h. Filtration and evaporation to dryness gave Compound 1c as a brown solid (1.18 g; 100%). $^1$H-NMR (300 MHz, CDCl$_3$): δ 7.82 (s, 1H), 7.09-7.12 (d, 2H), 7.00-7.03 (d, 2H), 6.88-6.92 (d, 2H), 6.82-6.85 (d, 2H), 3.81 (s, 3H), 3.78 (3H, s), 3.63 (s, 2H); MS: m/z 340.2 (M+H)$^+$.

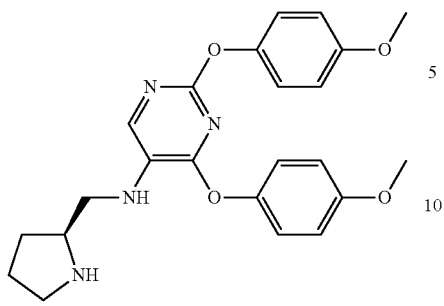

Cpd 1

A. 2-(S)-{[2,4-Bis-(4-methoxyphenoxy)pyrimidin-5-ylamino]-methyl}pyrrolidine-1-carboxylic acid tert-butyl ester (2a) To a solution of Compound 1c (0.29 g; 0.85 mmol), N-t-Boc-L-prolinal (0.17 g; 0.85 mmol) in DCE (5 mL) was added acetic acid (0.1 mL) and the reaction mixture was stirred at room temperature under a nitrogen atmosphere for 1 h. To the reaction mixture was then added NaBH(OAc)$_3$ (0.27 g; 1.28 mmol) and the reaction was continually stirred for 20 h. The resultant mixture was partitioned between dichloromethane and saturated NaHCO$_3$ $_{(aq)}$. The organic layer was washed with brine, dried over Na$_2$SO$_4$, filtered, and the solvent evaporated in vacuo to yield a crude oil. The crude oil was purified by flash column chromatography (eluant, EtOAc/hexanes gradient) to afford Compound 2a as a colorless gel (0.5 g; 100%). $^1$H-NMR (300 MHz, CDCl$_3$): δ 7.64 (s, 1H), 7.05-7.13 (m, 2H), 6.98-7.03 (m, 2H), 6.82-6.90 (m, 4H), 4.09-4.28 (m, 1H), 3.81 (s, 3H), 3.78 (s, 3H), 3.27-3.68 (m, 4H), 1.74-2.11 (m, 4H), 1.46 (s, 9H); MS: m/z 523.3 (M+H)$^+$.

B. [2,4-Bis-(4-methoxyphenoxy)pyrimidin-5-yl]pyrrolidin-2-(S)-ylmethylamine (Cpd 1) To a solution of Compound 2a (0.16 g, 0.3 mmol) in DCM (1 mL) was added TFA (1 mL) and the mixture was stirred at room temperature for 2 h. Concentration of the reaction mixture and purification by reverse phase HPLC afforded Compound 1 as a TFA salt. MS: m/z 423.3 (M+H)$^+$.

Following the procedure described above for Example 2 and substituting the appropriate reagents, starting materials and purification methods known to those skilled in the art, the following compounds of the present invention were prepared:

| Cpd | MS (M + H)$^+$ | Cpd | MS (M + H)$^+$ |
|---|---|---|---|
| 6 | 423.1 | 8 | 423.1 |
| 14 | 409.2 | 16 | 437.2 |
| 18 | 437.2 | 23 | 423.2 |
| 26 | 437.2 | 32 | 439.2 |
| 34 | 451.2 | 35 | 451.2 |

Cpd 25: Using an adaptation of the procedure described above for Example 2, substituting 2,4-bis-(4-fluoro-phenoxy)-pyrimidin-5-ylamine (prepared in an analogous manner to Compound 1c of Example 1, substituting 4-fluorophenol for 4-methoxyphenol in procedure A) for Compound 1c in Procedure A, the title compound was obtained. $^1$H NMR (300 MHz, CDCl$_3$): δ 10.02 (br. s., 1H), 9.27 (br. s., 1H), 7.74 (s, 1H), 6.89-7.04 (m, 8H), 3.90 (br. s., 1H), 3.41-3.60 (m, 2H), 3.12-3.40 (m, 2H), 2.11-2.26 (m, 1H), 1.88-2.11 (m, 2H), 1.68-1.87 (m, 1H).

Cpd 27: Using an adaptation of the procedure described above for Example 2, substituting 2,4-bis-(2-bromo-phenoxy)-pyrimidin-5-ylamine (prepared in an analogous manner to Compound 1c of Example 1, substituting 2-bromophenol for 4-methoxyphenol in Procedure A) for Compound 1c in Procedure A, the title compound was obtained. $^1$H NMR (300 MHz, MeOH-d$_4$): δ 7.95 (s, 1H), 7.45-7.6 (m, 2H), 6.95-7.35 (m, 6H), 3.95 (m, 1H), 3.5 (m, 2H), 3.3 (m, 2H), 2.3 (m, 1H), 2.1 (m, 2H), 1.85 (m, 1H); MS: m/z 521.1 (M+H)$^+$.

Example 3

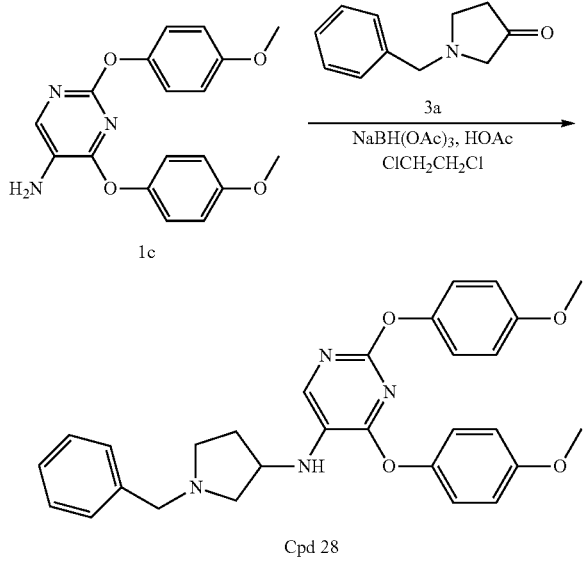

Cpd 28

A. (1-Benzyl-pyrrolidin-3-yl)-[2,4-bis-(4-methoxy-phenoxy)-pyrimidin-5-yl]-amine (Cpd 28) Using an adaptation of the method described in Procedure A of Example 2, substituting 1-benzyl-pyrrolidin-3-one (Compound 3a) for N-t-Boc-L-prolinal, the title Compound 28 was obtained. $^1$H-NMR (300 MHz, CDCl$_3$): δ 10.05 (br. s, 2H), 7.76 (s, 1H), 7.41 (s, 5H), 6.98 (d, 2H), 6.91 (d, 2H), 6.76 (d, 4H), 4.00-4.37 (m, 4H), 3.76 (s, 6H), 3.64-3.68 (m, 1H), 3.29-3.35 (m, 1H), 2.99-3.09 (m, 1H), 2.61-2.69 (m, 1H), 2.15-2.25 (m, 1H); MS: m/z 499.2 (M+H)$^+$.

Following the procedure described above for Example 3 and substituting the appropriate reagents, starting materials and purification methods known to those skilled in the art, the following compounds of the present invention were prepared:

| Cpd | MS (M + H)$^+$ | Cpd | MS (M + H)$^+$ |
|---|---|---|---|
| 15 | 449.2 | 28 | 499.2 |
| 29 | 513.2 | 30 | 525.2 (M − 1) |
| 31 | 437.2 | 33 | 513.2 |
| 39 | 467.2 | 41 | 445.2 |
| 42 | 465.1 | | |

Example 4

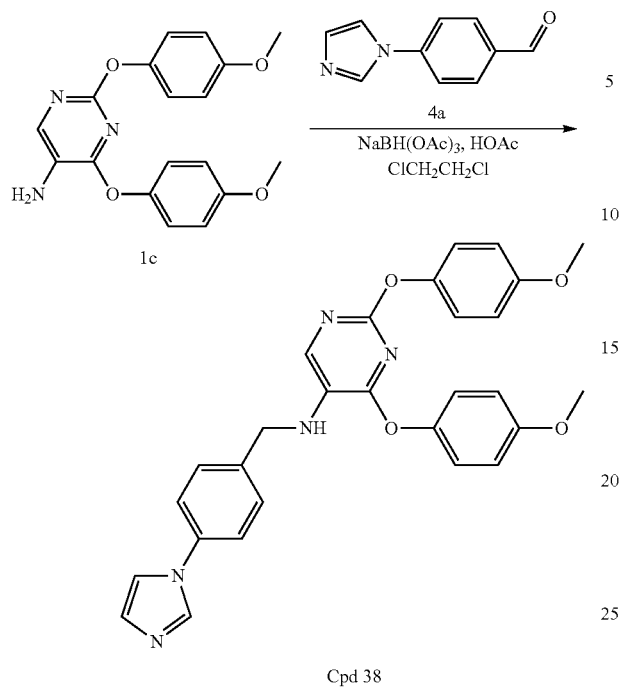

A. [2,4-Bis-(4-methoxy-phenoxy)-pyrimidin-5-yl]-(4-imidazol-1-yl-benzyl)-amine (Cpd 38) Using an adaptation of the method described in Procedure A of Example 2, substituting 4-imidazol-1-yl-benzaldehyde (Compound 4a) for N-t-Boc-L-prolinal, the title Compound 38 was obtained. $^1$H-NMR (300 MHz, CDCl$_3$): δ 12.45 (br. s., 2H), 9.01 (s, 1H), 7.58-7.68 (m, 2H), 7.44-7.57 (m, 5H), 6.96-7.09 (m, 2H), 6.85-6.96 (m, 2H), 6.78-6.85 (m, 2H), 6.70-6.78 (m, 2H), 4.51 (s, 2H), 3.78 (s, 3H), 3.75 (s, 3H); MS: m/z 496.2 (M+H)$^+$.

Following the procedure described above for Example 4 and substituting the appropriate reagents, starting materials and purification methods known to those skilled in the art, the following compounds of the present invention were prepared:

| Cpd | MS (M + H)$^+$ |
|---|---|
| 40 | 431.1 |
| 44 | 437.1 |
| 43 | 420.1 |

Example 5

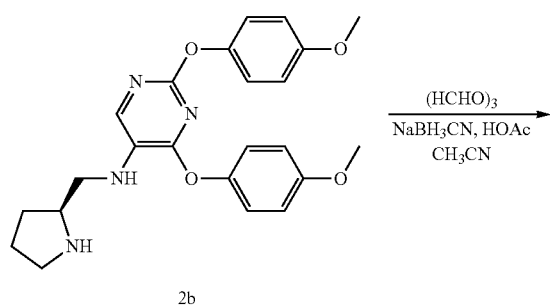

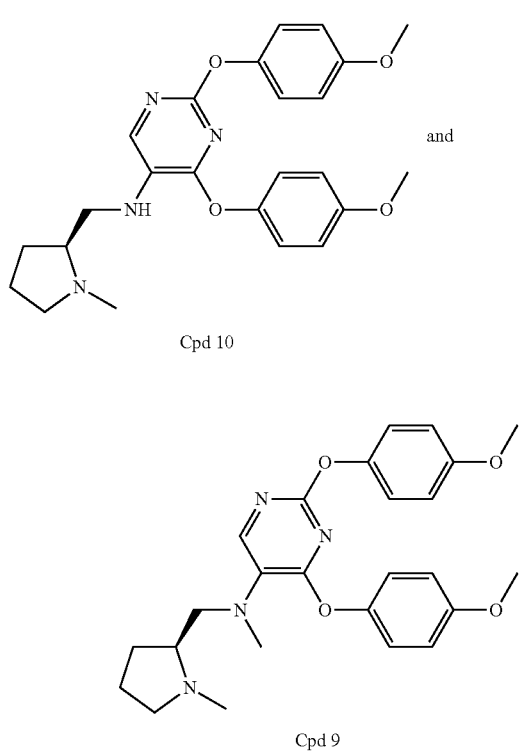

A. [2,4-Bis-(4-methoxy-phenoxy)-pyrimidin-5-yl]-(1-methyl-pyrrolidin-2-(S)-ylmethyl)-amine (Cpd 10) To a solution of Compound 2b (0.13 g; 0.3 mmol) in CH$_3$CN (5 mL) and HOAc (0.08 mL) was added formalin (37%, 0.03 mL) and NaBH$_3$CN (0.08 g; 1.14 mmol). After stirring at room temperature for 30 min, the mixture was concentrated and the residue was partitioned between 1N NaOH$_{(aq)}$ and EtOAc. The isolated organic phase was concentrated, and purified by HPLC to give Compound 10. $^1$H-NMR (300 MHz, CDCl$_3$): δ 7.85 (s, 1H), 7.00-7.03 (d, 2H), 6.93-6.96 (d, 2H), 6.78-6.80 (d, 4H), 3.80-3.96 (m, 2H), 3.79 (s, 3H), 3.78 (s, 3H), 3.56-3.68 (m, 2H), 2.96 (s, 3H), 2.91-3.05 (m, 1H), 2.29-2.42 (m, 1H), 2.09-2.23 (m, 2H), 1.93-2.04 (m, 1H); MS: m/z 437.2 (M+H)$^+$.

B. 2,4-Bis-(4-methoxyphenoxy)pyrimidin-5-yl]methyl-(1-methylpyrrolidin-2-(S)-ylmethyl)amine (Cpd 9) To a solution of Compound 2b (0.16 g; 0.38 mmol) in CH$_3$CN (5 mL) and HOAc (0.08 mL) was added formalin (37%, 0.15 mL) and NaBH$_3$CN (0.08 g; 1.14 mmol). After stirring at room temperature for 30 min, the mixture was concentrated and the residue was partitioned between 1N NaOH$_{(aq)}$ and EtOAc. The isolated organic phase was evaporated and purified by HPLC to give Compound 9. $^1$H-NMR (300 MHz, CDCl$_3$): δ 7.93 (s, 1H), 7.02-7.05 (d, 2H), 6.92-6.97 (d, 2H), 6.86-6.89 (d, 2H), 6.80-6.83 (d, 2H), 4.34-4.44 (m, 1H), 3.81 (s, 3H), 3.78 (s, 3H), 3.51-3.93 (m, 4H), 3.41 (s, 3H), 2.95 (s, 3H), 2.56-2.65 (m, 1H), 2.36-2.19 (m, 2H), 1.96-2.09 (m, 1H); MS: m/z 450.2 (M)$^+$.

Example 6

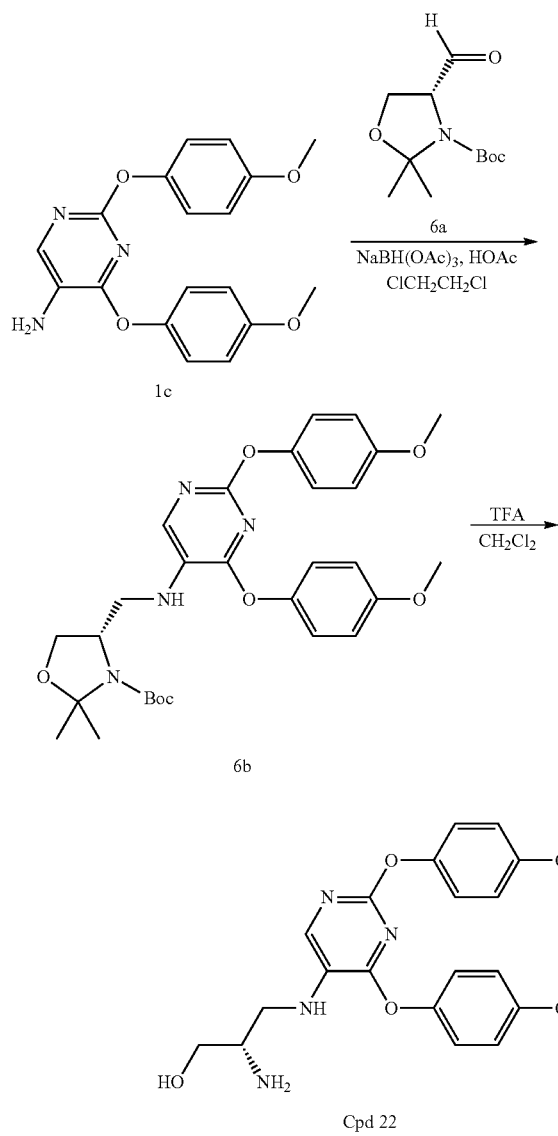

A. 2-(S)-{[4-(4-Methoxy-phenoxy)-[2,5']bipyrimidinyl-5-ylamino]-methyl}-pyrrolidine-1-carboxylic acid tert-butyl ester (6b) Using an adaptation of the method described in Procedure A of Example 2, substituting 4-formyl-2,2-dimethyl-oxazolidine-3-carboxylic acid tert-butyl ester (Compound 6a) for N-t-Boc-L-prolinal, the title Compound 6b was obtained. MS: m/z 553.3 (M+H)$^+$.

B. 2-(S)-Amino-3-[2,4-bis-(4-methoxy-phenoxy)-pyrimidin-5-ylamino]-propan-1-ol (Cpd 22) Using an adaptation of the method described in Procedure B of Example 2, substituting Compound 6b for Compound 2a, the title Compound 22 was obtained as a TFA salt. MS: m/z 413.2 (M+H)$^+$.

Following the procedure described above for Example 6 and substituting the appropriate reagents, starting materials and purification methods known to those skilled in the art, the following compounds of the present invention were prepared:

| Cpd | MS (M + H)$^+$ |
|---|---|
| 11 | 413.2 |

Example 7

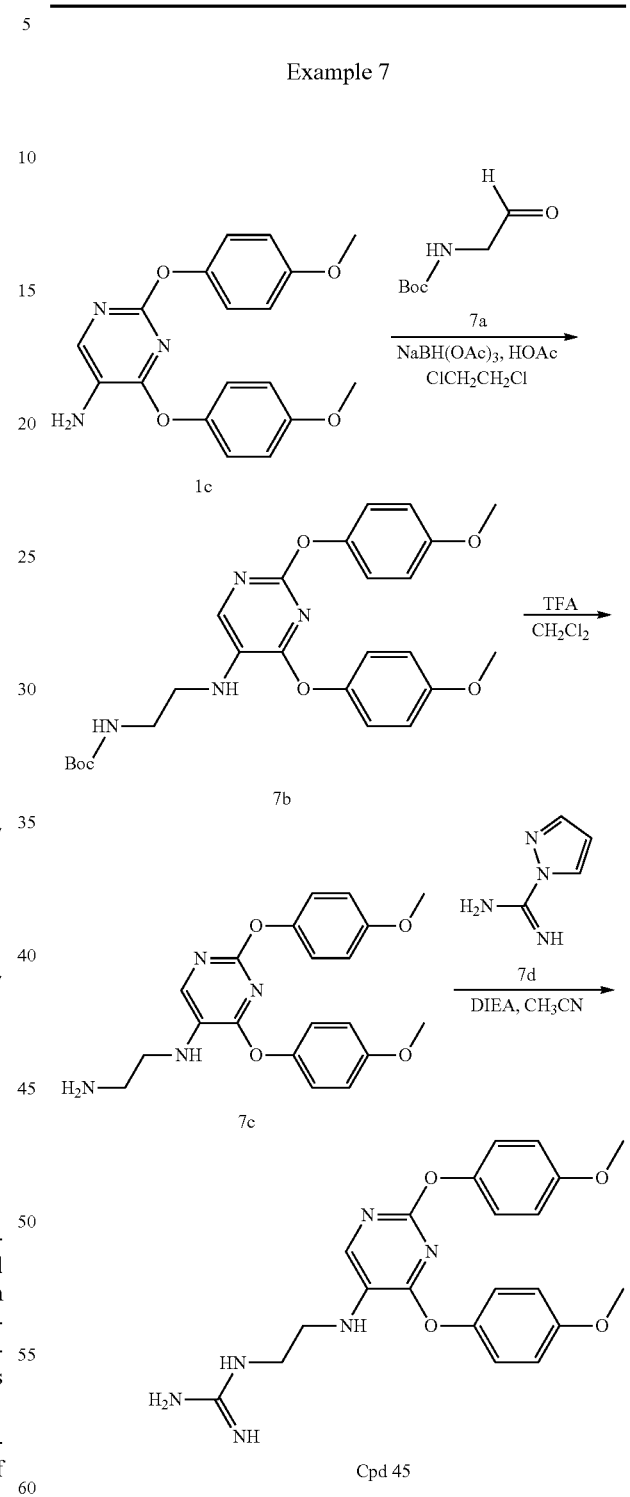

A. {2-[2,4-Bis-(4-methoxy-phenoxy)-pyrimidin-5-ylamino]-ethyl}-carbamic acid tert-butyl ester (7b) Using an adaptation of the method described in Procedure A of Example 2, substituting (2-oxo-ethyl)-carbamic acid tert-butyl ester (Compound 7a) for N-t-Boc-L-prolinal, the title Compound 7b was obtained. MS: m/z 483.2 (M+H)$^+$.

B. N$^1$-[2,4-Bis-(4-methoxy-phenoxy)-pyrimidin-5-yl]-ethane-1,2-diamine (7c) To a solution of Compound 7b (74 mg; 0.15 mmol) in CH$_2$Cl$_2$ (3 mL) was added TFA (0.4 mL) at ambient temperature. The mixture was stirred at room temperature for 20 h. The resultant mixture was concentrated in vacuo. The residue was partitioned between CH$_2$Cl$_2$ and saturated NaHCO$_3$ (aq). The aqueous phase was extracted with CH$_2$Cl$_2$. The combined organic extracts were dried over Na$_2$SO$_4$, filtered, and the filtrate was concentrated under reduced pressure to give Compound 7c (42 mg; 73% yield). The crude product was used directly in the next step without further purification. MS: m/z 383.2 (M+H)$^+$.

C. N-{2-[2,4-Bis-(4-methoxy-phenoxy)-pyrimidin-5-ylamino]-ethyl}-guanidine (Cpd 45) To a solution of Compound 7c (42 mg; 0.11 mmol) in acetonitrile (10 mL) was added 1H-pyrazole-1-carboxamidine hydrochloride (Compound 7d) (16 mg; 0.11 mmol) and N,N-diisopropylethylamine (0.22 mmol). The reaction mixture was stirred at room temperature for 3 d. The resultant mixture was partitioned between EtOAc and H$_2$O. The organic phase was washed with H$_2$O, and dried over Na$_2$SO$_4$. The mixture was filtered and the solvent evaporated under reduced pressure to give a residue, which was purified by reverse phase HPLC (eluting with a CH$_3$CN—H$_2$O gradient containing 0.5% TFA) to afford Compound 45 (11 mg; 15% yield) as a TFA salt. MS: m/z 425.2 (M+H)$^+$.

Example 8

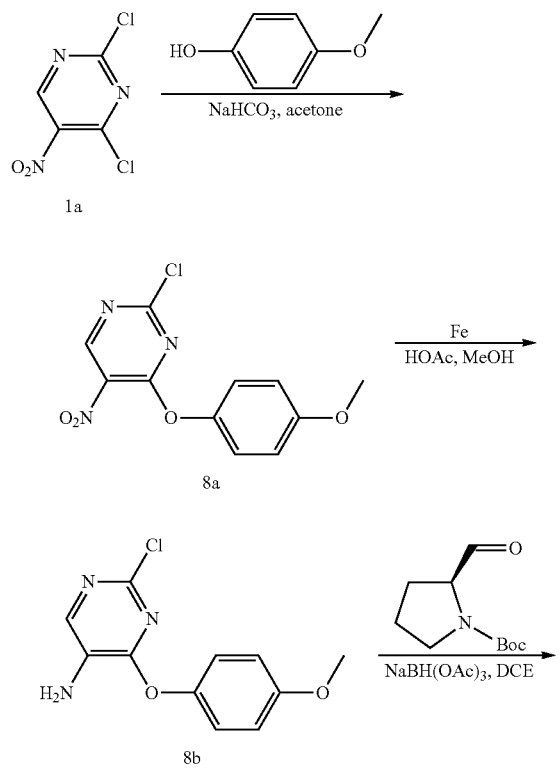

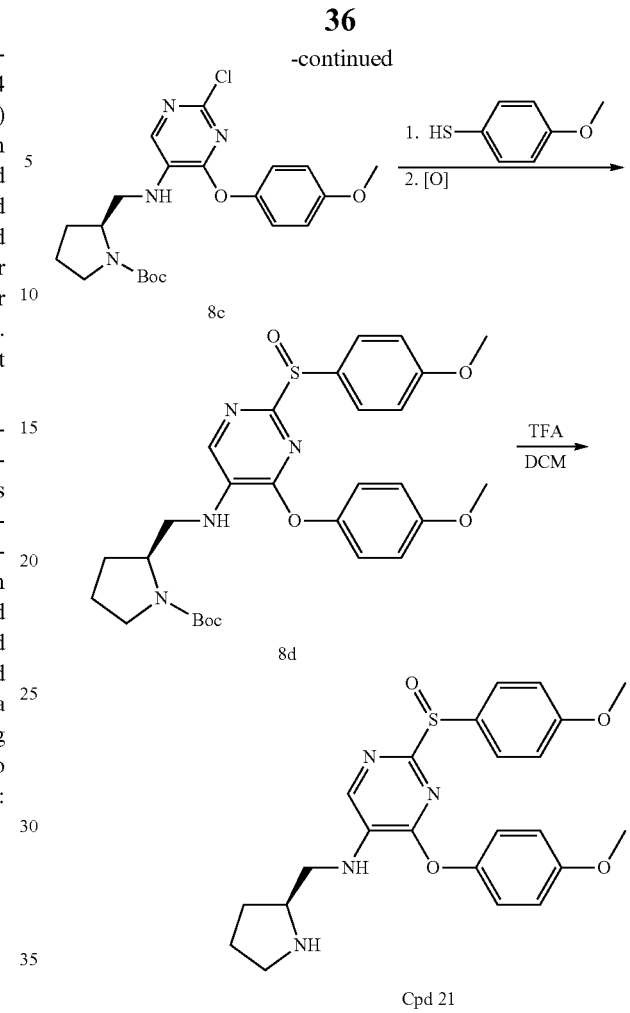

A. 2-Chloro-4-(4-methoxyphenoxy)-5-nitropyrimidine (8a) To a solution of Compound 1a (3 g; 15.5 mmol) in acetone (240 mL) at 0° C. was added a solution of 4-methoxyphenol (1.94 g; 15.5 mmol) in 1N NaHCO$_3$ aqueous solution (15.5 mL; 15.5 mmol) and H$_2$O (60 mL), dropwise. Upon completion of the addition, the reaction mixture was allowed to warm to room temperature slowly and stirred at room temperature for 20 h. The reaction mixture was concentrated and the residue was taken up in EtOAc, washed sequentially with 1N NaOH$_{(aq)}$ and brine, and dried over MgSO$_4$. The mixture was filtered and concentrated to afford Compound 8a as a brown solid. $^1$H-NMR (300 MHz, CDCl$_3$): δ 9.15 (s, 1H), 7.10-7.13 (d, 2H), 6.95-6.99 (d, 2H), 3.85 (s, 3H); MS: m/z 282.0 (M+H)$^+$.

B. 2-Chloro-4-(4-methoxyphenoxy)-pyrimidin-5-ylamine (8b) To a solution of Compound 8a (0.42 g; 1.5 mmol) in HOAc (5.5 mL) and MeOH (6 mL) was added in portions iron powder (0.25 g; 4.5 mmol). The mixture was heated at 65° C. for 2.5 h. Upon removal of the solvent by evaporation, the residue was partitioned between 1N NaOH$_{(aq)}$ and DCM, filtered through a pad of diatomaceous earth and the phases were separated. The organic phase was washed sequentially with water and brine, and dried over Na$_2$SO$_4$. Concentration of the mixture gave Compound 8b (0.49 g; 100%). $^1$H-NMR (300 MHz, CDCl$_3$): δ 7.92 (s, 1H), 7.09-7.12 (d, 2H), 6.92-6.95 (d, 2H), 3.92 (s, 2H), 3.83 (s, 3H); MS: m/z 252.1 (M+H)$^+$.

C. 2-(S)-{[2-Chloro-4-(4-methoxyphenoxy)-pyrimidin-5-ylamino]-methyl}-pyrrolidine-1-carboxylic acid tert-butyl ester (8c) To a solution of the Compound 8b (1.65 g; 6.6 mmol) and N-tert-Boc-L-prolinal (1.6 g; 7.8 mmol) in DCE (40 mL) was added NaBH(OAc)$_3$ (1.12 g; 10 mmol). The resulting mixture was stirred at room temperature under nitrogen atmosphere for 16 h. Upon removal of the solvents, the residue was partitioned between saturated NaHCO$_3$ $_{(aq)}$ and EtOAc, the EtOAc extract was washed with brine and dried over MgSO$_4$. Evaporation of the solvent and purification by preparative TLC (eluent, EtOAc/hexanes:3/7) gave Compound 8c as a yellow oil (2.51 g; 87%). $^1$H-NMR (300 MHz, CDCl$_3$): δ 7.64 (s, 1H), 6.99-7.02 (d, 2H), 6.82-6.85 (d, 2H), 4.09-4.22 (m, 1H), 3.78 (s, 3H), 3.27-3.66 (m, 4H), 1.73-2.09 (m, 3H), 1.44-1.55 (m, 1H); MS: m/z 523.3 (M+H)$^+$.

D. 2-(S)-{[2-(4-Methoxybenzenesulfinyl)-4-(4-methoxyphenoxy)-pyrimidin-5-ylamino]-methyl}pyrrolidine-1-carboxylic acid tert-butyl ester (8d) A mixture of Compound 8c (0.05 g; 0.11 mmol) and 4-methoxybenzenethiol (0.073 mL; 0.57 mmol) in 2-propanol (3.5 mL) was heated to reflux for 20 h. After cooling to room temperature, air was bubbled through the mixture for 20 h. Concentration of the reaction mixture under reduced pressure gave Compound 8d, which was used in the next step without further purification. MS: m/z 555.2 (M+H)$^+$.

E. [2-(4-Methoxybenzenesulfinyl)-4-(4-methoxyphenoxy)-pyrimidin-5-yl]-pyrrolidin-2-(S)-ylmethylamine (Cpd 21) To a solution of Compound 8d (0.13 g; 0.24 mmol) in DCM (1 mL) was added TFA (1 mL) and the mixture was stirred at room temperature for 1 h. The mixture was concentrated and purified by reverse phase HPLC to afford Compound 21 as a TFA salt. $^1$H-NMR (300 MHz, CDCl$_3$): δ 7.73 (s, 1H), 7.13-7.16 (d, 2H), 7.06-7.10 (d, 2H), 6.67-6.73 (m, 4H), 4.04-4.18 (m, 1H), 3.84 (s, 3H), 3.82 (s, 3H), 3.53-3.75 (m, 2H), 3.27-3.47 (m, 2H), 1.99-2.30 (m, 3H), 1.70-1.86 (m, 1H); MS: m/z 454.9 (M+H)$^+$.

Example 9

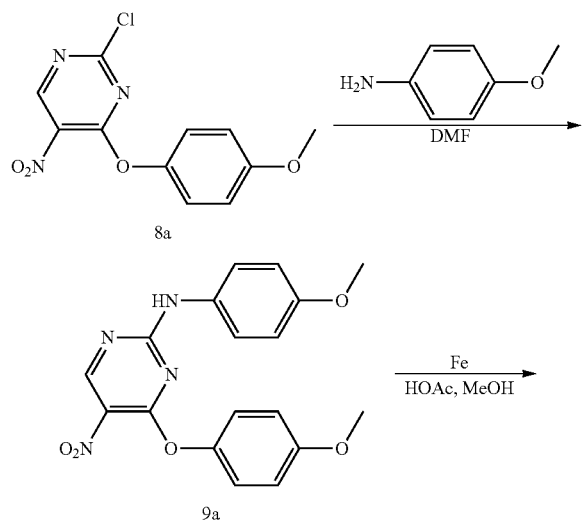

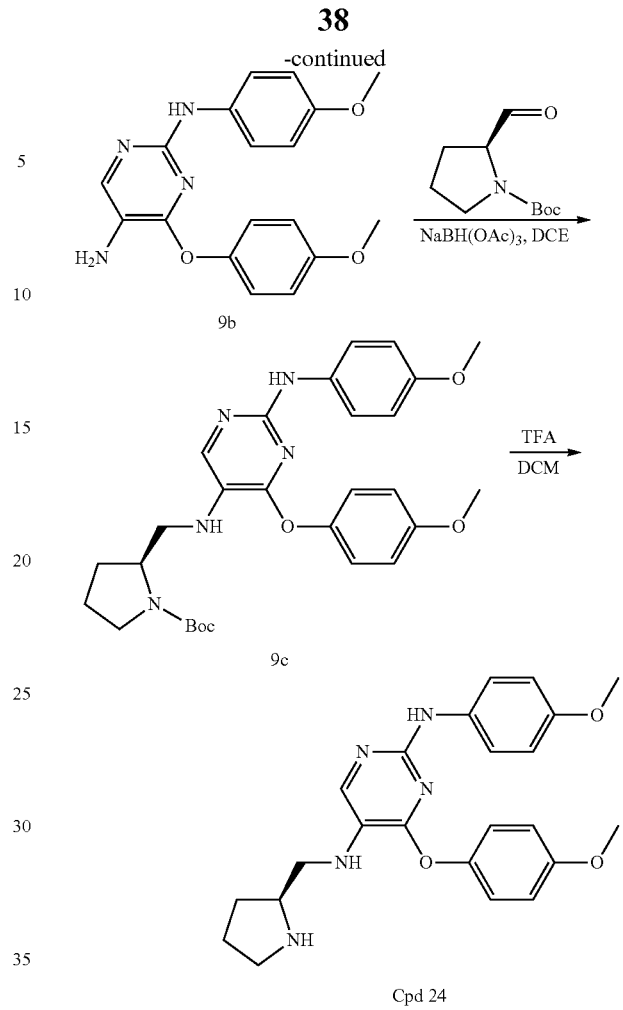

A. [4-(4-Methoxy-phenoxy)-5-nitro-pyrimidin-2-yl]-(4-methoxy-phenyl)-amine (9a) A solution of Compound 8a (0.14 g; 0.5 mmol) and 4-methoxy-phenylamine (0.31 g; 2.5 mmol) in DMF (1 mL) was heated at 60° C. for 25 h. The reaction was quenched by addition of saturated NH$_4$Cl$_{(aq)}$, extracted with EtOAc, and the combined extracts dried over Na$_2$SO$_4$. The mixture was filtered, concentrated, and purified by flash column chromatography (eluent, EtOAc/hexanes:1/1) to give Compound 9a. $^1$H-NMR (300 MHz, CDCl$_3$): δ 9.12 (s, 1H), 7.34-7.52 (m, 2H), 6.86-6.96 (m, 2H), 6.74-6.83 (m, 4H), 4.54 (s, 1H), 3.85 (s, 3H), 3.81 (s, 3H); MS: m/z 368.1 (M)$^+$.

B. 4-(4-Methoxy-phenoxy)-N$^2$-(4-methoxy-phenyl)-pyrimidine-2,5-diamine (9b) Using an adaptation of the method described in Procedure B of Example 8, substituting Compound 9a for Compound 8a, the title Compound 9b was obtained. MS: m/z 338.1 (M)$^+$.

C. 2-(S)-{[4-(4-Methoxyphenoxy)-2-(4-methoxyphenylamino)-pyrimidin-5-ylamino]-methyl}-pyrrolidine-1-carboxylic acid tert-butyl ester (9c) Using an adaptation of the method described in Procedure C of Example 8, substituting Compound 9b for Compound 8b, the title Compound 9c was obtained. MS: m/z 522.0 (M+H)$^+$.

D. 4-(4-Methoxyphenoxy)-N$^2$-(4-methoxyphenyl)-N$^6$-pyrrolidin-2-(S)-ylmethyl-pyrimidine-2,5-diamine (Cpd 24) A solution of Compound 9c (0.1 g; 0.18 mmol) in DCM (1 mL) was added TFA (1 mL) and the mixture was stirred at room temperature for 1 h. The reaction mixture was concentrated to a residue, which was purified by reverse phase HPLC to afford Compound 24 as a TFA salt. $^{1}$H-NMR (300 MHz, CDCl$_3$): δ 7.40 (s, 1H), 6.97-7.00 (d, 2H), 6.76-6.85 (m, 4H), 6.49-6.52 (d, 2H), 3.86-4.00 (m, 1H), 3.78 (s, 3H), 3.67 (s, 3H), 3.25-3.56 (m, 4H), 2.03-2.36 (m, 3H), 1.72-1.87 (m, 1H); MS: m/z 422.0 (M+H)$^{+}$.

Example 10

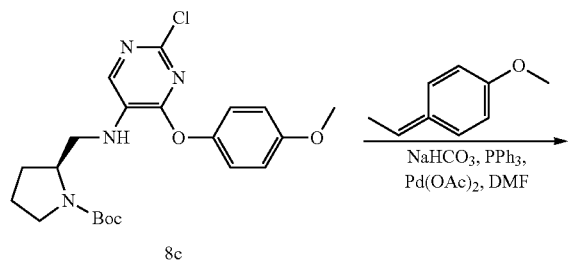

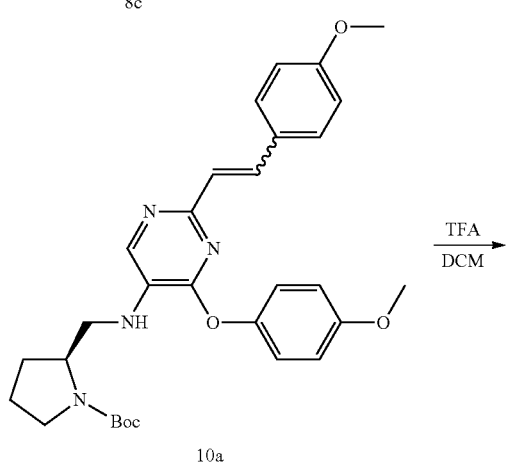

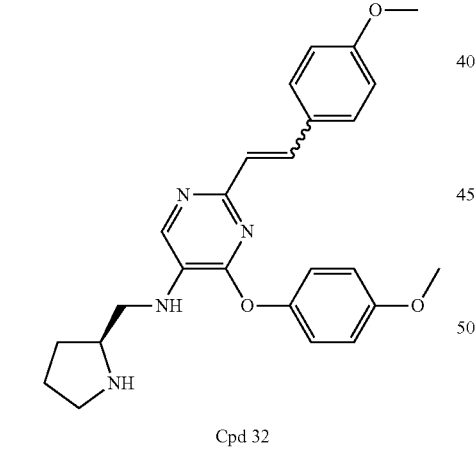

A. 2-(S)-({4-(4-Methoxyphenoxy)-2-[2-(4-methoxyphenyl)vinyl]-pyrimidin-5-ylamino}-methyl)pyrrolidine-1-carboxylic acid tert-butyl ester (10a) A mixture of 1-methoxy-4-vinyl-benzene (0.16 mL; 1.17 mmol), Compound 8c (0.11 g; 0.25 mmol), NaHCO$_3$ (0.15 g; 1.84 mmol), PPh$_3$ (0.12 g; 0.46 mmol) and Pd(OAc)$_2$ (0.01 g; 0.046 mmol) in DMF (1 mL) in a sealed tube was heated at 130° C. for 16 h. The reaction mixture was diluted with water, extracted, and purified by flash column chromatography (eluent, EtOAc/hexanes:1/1) to give Compound 10a as a mixture of its trans- and cis-stereoisomers (0.03 g; 23%). MS: m/z 533.5 (M+H)$^{+}$.

B. {4-(4-Methoxyphenoxy)-2-[2-(4-methoxyphenyl)vinyl]-pyrimidin-5-yl}-pyrrolidin-2-(S)-ylmethylamine (10b) To a solution of Compound 10a (0.048 g; 0.09 mmol) in DCM (1 mL) was added TFA (1 mL) and the mixture was stirred at room temperature for 1 h. The mixture was concentrated and purified by reverse phase HPLC to afford Compound 10b as a mixture of its trans- and cis-stereoisomers. MS: m/z 432.9 (M+H)$^{+}$.

Example 11

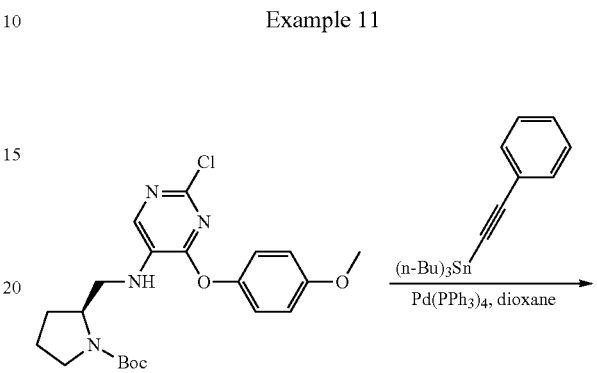

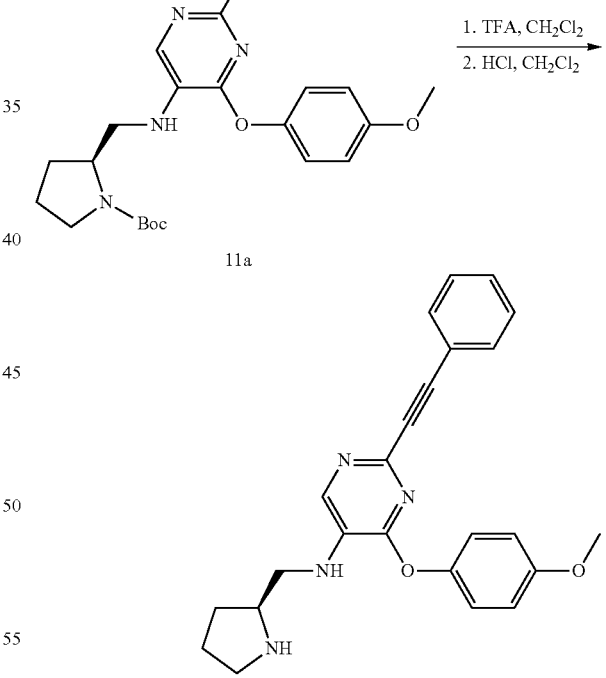

A. 2-(S)-{[4-(4-Methoxy-phenoxy)-2-phenylethynyl-pyrimidin-5-ylamino]-methyl}-pyrrolidine-1-carboxylic acid tert-butyl ester (11a) To a teflon-lined septum sealed Schlenk tube, a mixture of Compound 8c (214 mg; 0.49 mmol), tributyl-phenylethynyl-stannane (289 mg; 0.739 mmol) and tetrakis-(triphenylphosphine)palladium(0) (57 mg, 0.049 mmol) in dioxane (1.0 mL) was added and the mixture was irradiated in a microwave reactor at 150° C. for 30 min. The resultant mixture was diluted with EtOAc and washed with saturated NH₄Cl$_{(aq)}$ and water. The organic phase was washed with H₂O and then dried over Na₂SO₄. The mixture was filtered and the filtrate was evaporated under reduced pressure to give a crude material. The crude material was purified by flash column chromatography (SiO₂, eluting with a heptane-EtOAc gradient) to afford Compound 11a (120 mg; 49% yield). ¹H-NMR (400 MHz, CDCl₃): δ 7.84-7.98 (m, 1H), 7.52-7.60 (m, 2H), 7.29-7.34 (m, 3H), 7.08-7.19 (m, 2H), 6.89-6.99 (m, 2H), 5.98 (br. s., 0.6H), 4.97 (br. s., 0.4H), 4.18-4.38 (m, 1H), 3.85 (s, 3H), 3.13-3.46 (m, 4H), 2.07-2.17 (m, 1H), 1.90-2.03 (m, 2H), 1.76-1.88 (m, 1H), 1.44-1.52 (m, 9H); MS: m/z 501.1 (M+H)⁺.

B. [4-(4-Methoxy-phenoxy)-2-phenylethynyl-pyrimidin-5-yl]-pyrrolidin-2-(S)-ylmethyl-amine (11b) To a solution of Compound 11a (118 mg; 0.236 mmol) in CH₂Cl₂ (3 mL) was added trifluoroacetic acid (0.3 mL) at ambient temperature. The reaction mixture was stirred at room temperature for 20 h. The reaction mixture was adjusted to pH 12 with 1 N NaOH$_{(aq)}$. The mixture was partitioned between CH₂Cl₂ and H₂O, and the organic phase was washed with H₂O, and dried over Na₂SO₄. The mixture was then filtered, and the filtrate was concentrated under reduced pressure. The residue was dissolved in CH₂Cl₂ (3 mL), and treated with 1.0 M HCl in Et₂O (0.24 mL; 0.24 mmol) at ambient temperature. The reaction mixture was stirred at room temperature for 20 h. The resultant mixture was concentrated in vacuo to afford a residue that was triturated with Et₂O. A solid was collected by filtration and dried to afford Compound 11b as a HCl salt (97 mg; 94% yield). HCl salt ¹H-NMR (400 MHz, DMSO-d₆): δ 8.94 (br. s., 1H), 8.54 (br. s., 1H), 8.13 (s, 1H), 7.48-7.55 (m, 2H), 7.37-7.46 (m, 2H), 7.14-7.21 (m, 2H), 6.99-7.06 (m, 2H), 6.45 (t, 1H), 3.80-3.88 (m, 1H), 3.79 (s, 3H), 3.49-3.57 (m, 2H), 3.16-3.28 (m, 2H), 2.07-2.21 (m, 1H), 1.84-2.05 (m, 2H), 1.63-1.78 (m, 1H); MS: m/z 401.1 (M+H)⁺.

Example 12

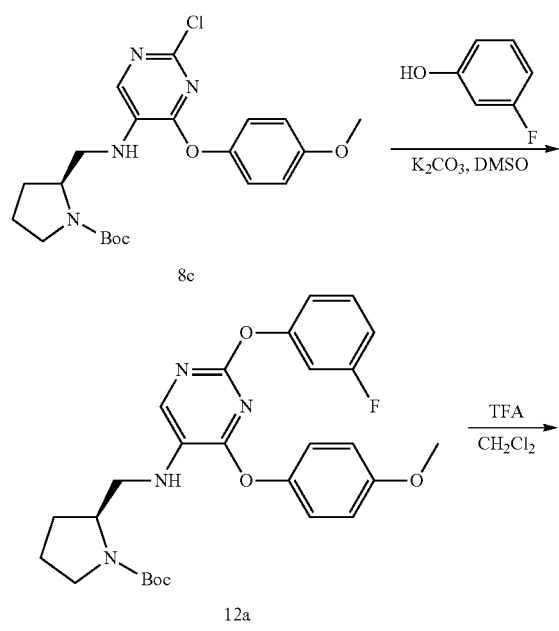

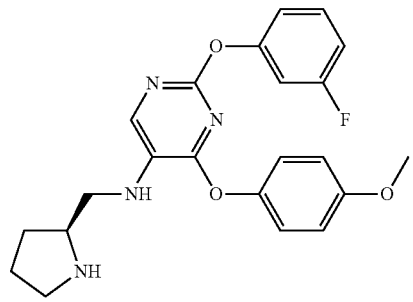

Cpd 48

A. 2-(S)-{[2-(3-Fluoro-phenoxy)-4-(4-methoxy-phenoxy)-pyrimidin-5-ylamino]-methyl}-pyrrolidine-1-carboxylic acid tert-butyl ester (12a) In a teflon-lined septum sealed Schlenk tube, a solution of Compound 8c (150 mg; 0.345 mmol), 3-fluoro-phenol (100 mg; 0.89 mmol) and K₂CO₃ (95 mg; 0.69 mmol) in DMSO (1 mL) was irradiated in a microwave reactor at 180° C. for 10 min. The Diluted the resultant mixture was diluted with Et₂O, and washed with saturated NH₄Cl$_{(aq)}$ and H₂O. The organic phase was isolated and washed sequentially with H₂O and brine, and then dried over Na₂SO₄. The mixture was filtered and the filtrate was evaporated under reduced pressure to give a crude material. The crude material was purified by flash column chromatography (SiO₂, eluting with a heptane-EtOAc gradient) to afford Compound 12a (35 mg; 20% yield).). ¹H-NMR (400 MHz, CDCl₃): δ 7.67-7.72 (m, 1H), 7.21-7.25 (m, 2H), 7.04-7.11 (m, 2H), 6.80-6.93 (m, 4H), 5.71 (br. s, 0.2H), 5.21 (br. s, 0.5H), 4.45 (br. s, 0.3H), 4.16-4.29 (m, 1H), 3.81 (s, 3H), 3.09-3.55 (m, 4H), 1.77-2.11 (m, 4H), 1.45-1.48 (m, 9H); MS: m/z 511.2 (M+H)⁺.

B. [2-(3-Fluoro-phenoxy)-4-(4-methoxy-phenoxy)-pyrimidin-5-yl]-pyrrolidin-2-(S)-ylmethyl-amine (Cpd 48) To a solution of Compound 12a (35 mg; 0.069 mmol) in CH₂Cl₂ (2 mL) was added trifluoroacetic acid (0.25 mL). The reaction was stirred at room temperature for 3 h and the solvent was evaporated in vacuo to give a crude material. The crude material was purified by reverse phase HPLC (eluant, CH₃CN—H₂O gradient) to afford Compound 48 (23 mg; 53% yield) as a TFA salt. ¹H-NMR (400 MHz, CDCl₃): δ 9.56 (br. s, 1H), 7.66 (s, 1H), 7.20-7.24 (m, 2H), 7.00-7.03 (m, 2H), 6.79-6.86 (m, 4H), 4.87 (br. s, 1H), 3.80-3.84 (m, 1H), 3.79 (s, 3H), 3.46 (br. s, 2H), 3.17-3.26 (m, 2H), 2.10-2.19 (m, 1H), 1.92-2.08 (m, 2H), 1.72-1.82 (m, 1H); MS: m/z 411.2 (M+H)⁺.

Following the procedure described above for Example 12 and substituting the appropriate reagents, starting materials and purification methods known to those skilled in the art, the following compounds of the present invention were prepared:

| Cpd | MS (M + H)⁺ | Cpd | MS (M + H)⁺ |
|---|---|---|---|
| 46 | 394.2 | 51 | 427.0 |
| 52 | 423.0 | 53 | 418.0 |
| 54 | 429.0 | | |

Example 13

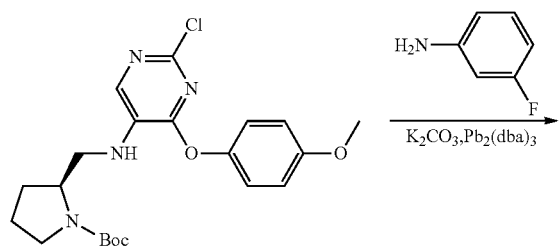

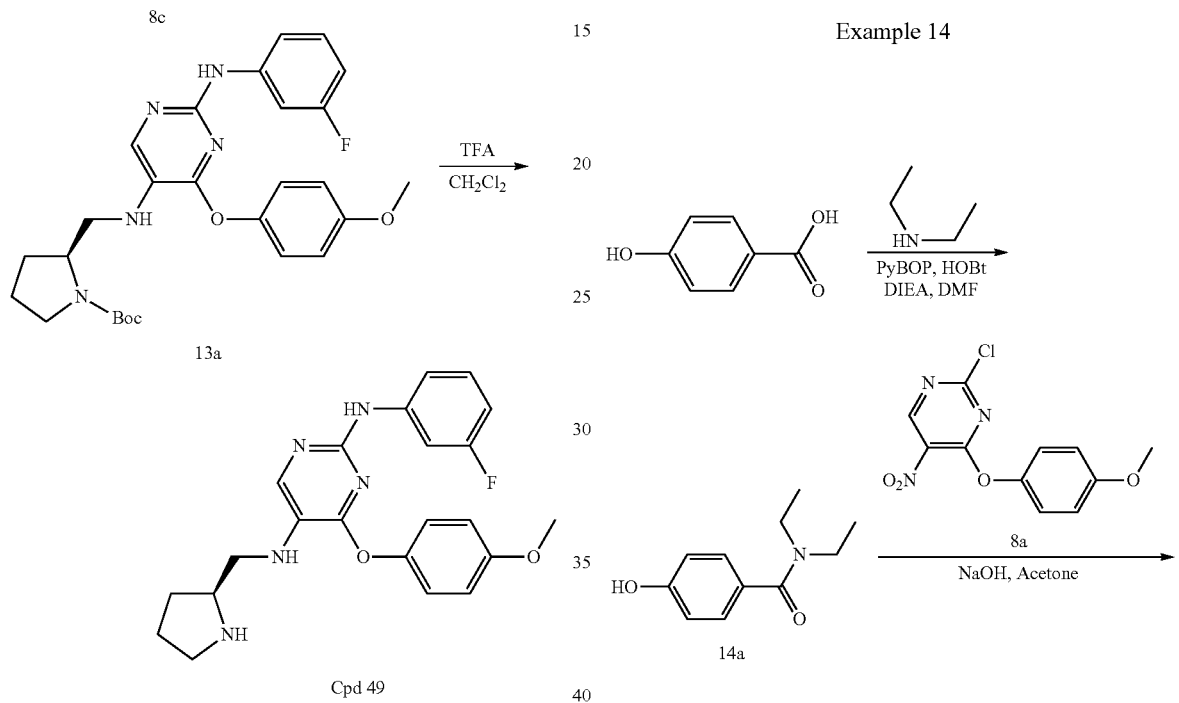

A. 2-(S)-{[2-(3-Fluoro-phenylamino)-4-(4-methoxy-phenoxy)-pyrimidin-5-ylamino]-methyl}-pyrrolidine-1-carboxylic acid tert-butyl ester (13a) To a dry Schlenk tube was added a mixture of Compound 8c (100 mg; 0.23 mmol), 3-fluoro-phenylamine (31 mg; 0.28 mmol), $K_2CO_3$ (44.5 mg; 0.32 mmol), 9,9-dimethyl-4,5-bis(diphenylphosphino)xanthene (8 mg; 0.014 mmol), and tris(dibenzylideneacetone)dipalladium(0) (4.2 mg; 0.0046 mmol). The tube was sealed with a teflon-lined septum, evacuated, and refilled with Argon. Toluene (0.8 mL) and several drops of water were added via syringe. The mixture was irradiated in a microwave reactor at 180° C. for 30 min. The resultant mixture was diluted with EtOAc, and washed sequentially with saturated $NH_4Cl_{(aq)}$ and $H_2O$. The organic phase was washed with $H_2O$, and then dried over $Na_2SO_4$. The mixture was filtered and the filtrate was evaporated under reduced pressure to give a crude material. The crude material was purified by flash column chromatography ($SiO_2$, eluant, heptane-EtOAc gradient) to afford Compound 13a (30 mg; 26% yield).). $^1$H-NMR (400 MHz, $CDCl_3$): δ 7.77 (s, 1H), 7.34 (dt, 1H), 7.10 (d, 2H), 7.02-7.08 (m, 1H), 6.98 (d, 2H), 6.79 (d, 1H), 6.74 (br. s, 1H), 6.52 (td, 1H), 4.76-4.80 (m, 0.5H), 4.16-4.26 (m, 1.5H), 3.86 (s, 3H), 3.11-3.52 (m, 4H), 1.87-2.10 (m, 4H), 1.23-1.30 (m, 9H); MS: m/z 510.3 (M+H)$^+$.

B. $N^2$-(3-Fluoro-phenyl)-4-(4-methoxy-phenoxy)-$N^5$-pyrrolidin-2-(S)-ylmethyl-pyrimidine-2,5-diamine (Cpd 49)

To a solution of Compound 13a (30 mg; 0.059 mmol) in $CH_2Cl_2$ (2 mL) was added trifluoroacetic acid (0.3 mL). The reaction was stirred at room temperature for 3 h and the solvent was evaporated in vacuo to give a crude material. The crude material was purified by reverse phase HPLC (eluant, $CH_3CN$—$H_2O$ gradient) to afford Compound 49 (25 mg; 67% yield) as a TFA salt. $^1$H-NMR (400 MHz, DMSO-$d_6$): δ 9.25 (s, 1H), 8.91 (br. s, 1H), 8.41 (br, 1H), 7.95 (s, 1H), 7.40 (dt, 1H), 7.15-7.19 (m, 2H), 7.02-7.13 (m, 4H), 6.53 (td, 1H), 5.34 (br. s, 1H), 3.81-3.86 (m, 1H), 3.79 (s, 3H), 3.20-3.39 (m, 4H), 2.10-2.17 (m, 1H), 1.87-1.99 (m, 2H), 1.66-1.73 (m, 1H); MS: m/z 410.3 (M+H)$^+$.

Example 14

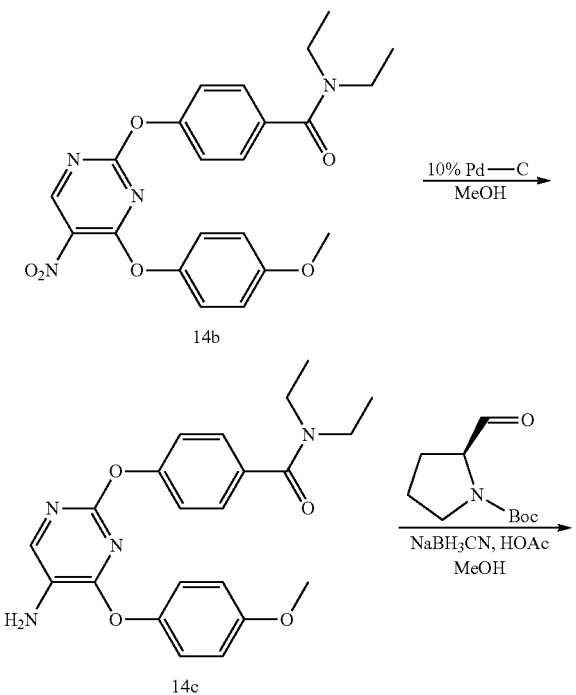

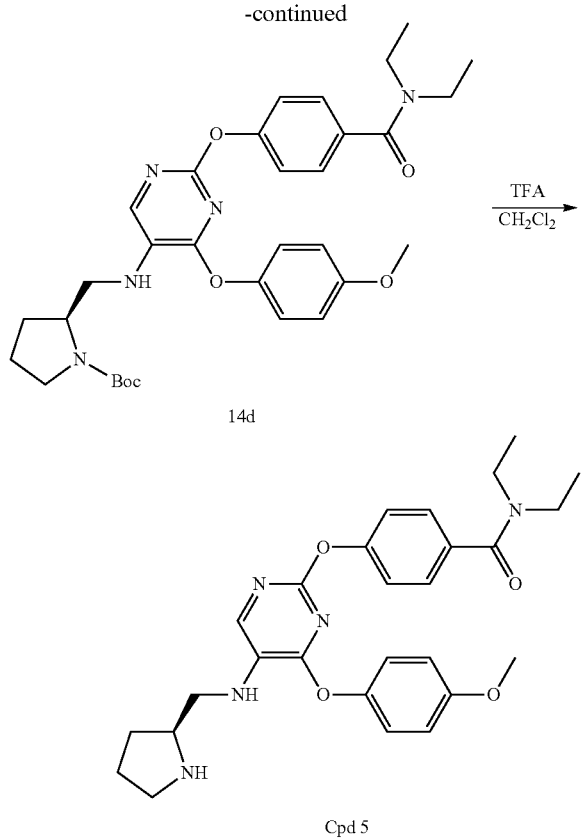

14d

Cpd 5

A. N,N-Diethyl-4-hydroxy-benzamide (14a) Under a nitrogen atmosphere, a mixture of 4-hydroxybenzoic acid (0.70 g; 5.0 mmol), $Et_2NH$ (1 mL; 10.0 mmol), (benzotriazol-1-yl-oxy)tripyrrolidinophosphonium hexafluorophosphate (5.2 g; 10.0 mmol), N-hydroxybenzotriazole (1.0 g; 7.5 mmol) and N,N-diisopropylethylamine (1.74 mL; 10.0 mmol) in DMF (8 mL) was stirred at room temperature for 20 h. The reaction was quenched with water, and then extracted with EtOAc. The organic phase was washed sequentially with 1N $HCl_{(aq)}$, saturated $NaHCO_{3\,(aq)}$ and brine, and dried over $Na_2SO_4$. The mixture was filtered, the filtrate concentrated, and the resultant residue was purified by flash column chromatography (eluent, EtOAc/hexanes:1/1) to afford Compound 14a as a white solid (0.45 g; 47% yield). $^1$H-NMR (300 MHz, $CDCl_3$): δ 9.22 (s, 1H), 7.17 (d, 2H), 6.72 (d, 2H), 3.33-3.51 (m, 4H), 1.10-1.26 (m, 6H); MS: m/z 194.1 $(M+H)^+$.

B. N,N-Diethyl-4-[4-(4-methoxy-phenoxy)-5-nitropyrimidin-2-yloxy]-benzamide (14b) To a solution of Compound 8a (0.14 g; 0.5 mmol) in acetone (4 mL) was added a solution of Compound 14a (0.11 g; 0.55 mmol) in 1N NaOH aqueous solution (0.55 mL; 0.55 mmol) and $H_2O$ (2 mL), dropwise. After completion of addition, the reaction mixture was allowed to warm to room temperature slowly and stirred at room temperature for 20 h. After concentration of the reaction mixture, the residue was extracted with EtOAc, washed with 1N $NaOH_{(aq)}$, brine, and dried over $MgSO_4$. Removal of the solvent followed by purification by flash column chromatography (eluent, EtOAc/hexanes:1/1) gave Compound 14b (0.09 g; 41%). MS: m/z 439.2 $(M+H)^+$.

C. 4-[5-Amino-4-(4-methoxy-phenoxy)-pyrimidin-2-yloxy]-N,N-diethyl-benzamide (14c) To a solution of Compound 14b (0.09 g; 0.2 mmol) in MeOH (10 mL) was added 10% Pd—C (0.1 g) and the reaction mixture was shaken in a Parr hydrogenator under a 32 psi hydrogen atmosphere for 20 h. Filtration and evaporation of the filtrate afforded Compound 14c (0.08 g; 98%). MS: m/z 409.2 $(M+H)^+$.

D. 2-(S)-{[2-(4-Diethylcarbamoyl-phenoxy)-4-(4-methoxy-phenoxy)-pyrimidin-5-ylamino]-methyl}-pyrrolidine-1-carboxylic Acid tert-butyl ester (14d) To a solution of Compound 14c (0.08 g; 0.196 mmol) and N-tert-Boc-L-prolinal (0.043 g; 0.215 mmol) in MeOH (1 mL) and HOAc (0.1 mL) was added $NaBH_3CN$ (0.025 g; 0.392 mmol). After stirring at room temperature for 4 h, the reaction was quenched by the addition of brine, the volatile components were removed by evaporation, and the residue was extracted with EtOAc. The organic phase was washed sequentially with 1 N $HCl_{(aq)}$, saturated $NaHCO_{3\,(aq)}$, and brine, and dried over $NaSO_4$. Concentration of the mixture followed by purification by preparative TLC (eluent, EtOAc/hexanes:1/1) afforded Compound 14d. MS: m/z 592.3 $(M+H)^+$.

E. N,N-Diethyl-4-{4-(4-methoxy-phenoxy)-5-[(pyrrolidin-2-(S)-ylmethyl)-amino]-pyrimidin-2-yloxy}-benzamide (14e) To a solution of Compound 14d (0.1 g; 0.19 mmol) in DCM (1 mL) was added TFA (1 mL) and the mixture was stirred at room temperature for 1 h. Concentration of the reaction mixture followed by purification by reverse phase HPLC afforded Compound 5 as a TFA salt. $^1$H-NMR (300 MHz, MeOH-$d_4$): δ 7.86 (d, 1H), 7.18-7.41 (m, 3H), 7.00-7.14 (m, 2H), 6.79-6.97 (m, 3H), 3.93 (br. s, 1H), 3.77 (d, 3H), 3.43-3.63 (m, 4H), 3.31-3.43 (m, 4H), 2.21-2.39 (m, 1H), 1.98-2.21 (m, 2H), 1.76-1.93 (m, 1H), 1.25 (br. s 3H), 1.14 (br. s, 3H); MS: m/z 492.3 $(M+H)^+$.

Compounds 1 through 54 of Formula (I) in Table 1 below were synthesized using the procedures described above.

TABLE 1

| Cpd | $R_1$ | Y | $R_2$ | $R_a$ | $R_3$ | Stereo chem |
|---|---|---|---|---|---|---|
| 1 | 4-methoxy-phenyl | O | 4-methoxy | H | pyrrolidin-2-yl methyl | (2S) |
| 2 | 4-methoxy-phenyl | O | 4-methoxy | H | piperidin-3-yl | (RS) |
| 3 | 4-methoxy-phenyl | O | 4-methoxy | H | 3-amino-cyclohexyl | (1RS, 3RS) |
| 4 | phenyl | ethynyl | 4-methoxy | H | pyrrolidin-2-yl methyl | (2S) |
| 5 | 4-diethyl amino carbonyl-phenyl | O | 4-methoxy | H | pyrrolidin-2-yl methyl | (2S) |
| 6 | 4-methoxy-phenyl | O | 4-methoxy | H | pyrrolidin-2-yl methyl | (2RS) |

TABLE 1-continued

| Cpd | R₁ | Y | R₂ | Rα | R₃ | Stereo chem |
|---|---|---|---|---|---|---|
| 7 | 4-methoxy-phenyl | O | 4-methoxy | H | pyrrolidin-2-yl methyl | (2R) |
| 8 | 4-methoxy-phenyl | O | 4-methoxy | methyl | 1-methyl-pyrrolidin-2-yl methyl | (2S) |
| 9 | 4-methoxy-phenyl | O | 4-methoxy | H | 1-methyl-pyrrolidin-2-yl methyl | (2S) |
| 10 | 4-methoxy-phenyl | O | 4-methoxy | H | 3-hydroxy-2-amino-propyl | (2R) |
| 11 | 4-methoxy-phenyl | O | 4-methoxy | H | 8-aza-bicyclo[3.2.1]oct-3-yl | (1RS, 5RS) |
| 12 | 4-methoxy-phenyl | O | 4-methoxy | H | piperidin-4-yl | |
| 13 | 4-methoxy-phenyl | O | 4-methoxy | H | azetidin-3-yl methyl | |
| 14 | 4-methoxy-phenyl | O | 4-methoxy | H | 1-aza-bicyclo[2.2.2]oct-3-yl | |
| 15 | 4-methoxy-phenyl | O | 4-methoxy | H | piperidin-3-ylmethyl | (3RS) |
| 16 | 4-methoxy-phenyl | O | 4-methoxy | H | 4-amino-cyclohexyl | |
| 17 | 4-methoxy-phenyl | O | 4-methoxy | H | piperidin-4-yl methyl | |
| 18 | 4-methoxy-phenyl | O | 4-methoxy | H | 2-methylamino-ethyl | |
| 19 | (4-methoxy-phenyl) | vinyl | 4-methoxy | H | pyrrolidin-2-yl methyl | (2S) |
| 20 | 4-methoxy-phenyl | S(O) | 4-methoxy | H | pyrrolidin-2-yl methyl | (2S) |
| 21 | 4-methoxy-phenyl | O | 4-methoxy | H | 3-hydroxy-2-amino-propyl | (2S) |
| 22 | 4-methoxy-phenyl | O | 4-methoxy | H | pyrrolidin-3-yl methyl | (3RS) |
| 23 | 4-methoxy-phenyl | NH | 4-methoxy | H | pyrrolidin-2-yl methyl | (2S) |
| 24 | 4-fluoro-phenyl | O | 4-fluoro | H | pyrrolidin-2-yl methyl | (2*S) |
| 25 | 4-methoxy-phenyl | O | 4-methoxy | H | piperidin-2-yl methyl | (2RS) |
| 26 | 2-bromo-phenyl | O | 2-bromo | H | pyrrolidin-2-yl methyl | (2S) |
| 27 | 4-methoxy-phenyl | O | 4-methoxy | H | 1-phenylmethyl-pyrrolidin-3-yl | (3RS) |
| 28 | 4-methoxy-phenyl | O | 4-methoxy | H | 1-phenylmethyl-piperidin-4-yl | |
| 29 | 4-methoxy-phenyl | O | 4-methoxy | H | 1-phenethyl-piperidin-4-yl | |
| 30 | 4-methoxy-phenyl | O | 4-methoxy | H | 1-methyl-piperidin-4-yl | |
| 31 | 4-methoxy-phenyl | O | 4-methoxy | H | morpholin-2-ylmethyl | (2RS) |
| 32 | 4-methoxy-phenyl | O | 4-methoxy | H | 1-phenylmethyl-piperidin-3-yl | (3RS) |
| 33 | 4-methoxy-phenyl | O | 4-methoxy | H | 2-(piperidin-4-yl)-ethyl | |
| 34 | 4-methoxy-phenyl | O | 4-methoxy | H | 2-(piperidin-3-yl)-ethyl | (3RS) |
| 35 | 4-methoxy-phenyl | O | 4-methoxy | H | 4-phenyl-piperidin-3-yl | (3RS, 4RS) |
| 36 | 4-methoxy-phenyl | O | 4-methoxy | H | pyrrolidin-3-yl | (3RS) |
| 37 | 4-methoxy-phenyl | O | 4-methoxy | H | 4-(imidazol-1-yl)-phenylmethyl | |
| 38 | 4-methoxy-phenyl | O | 4-methoxy | H | 4-diethylamino-but-2-yl | (2RS) |
| 39 | 4-methoxy-phenyl | O | 4-methoxy | H | pyridin-4-yl methyl | |

TABLE 1-continued

| Cpd | R₁ | Y | R₂ | $R_a$ | R₃ | Stereo chem |
|---|---|---|---|---|---|---|
| 40 | 4-methoxy-phenyl | O | 4-methoxy | H | 1-(pyridin-4-yl)-ethyl | (1RS) |
| 41 | 4-methoxy-phenyl | O | 4-methoxy | H | 1-methylcarbonyl-piperidin-4-yl | |
| 42 | 4-methoxy-phenyl | O | 4-methoxy | H | 1H-imidazol-2-yl methyl | |
| 43 | 4-methoxy-phenyl | O | 4-methoxy | H | thiazol-2-yl methyl | |
| 44 | 4-methoxy-phenyl | O | 4-methoxy | H | 2-guanidino-ethyl | |
| 45 | pyridin-3-yl | O | 4-methoxy | H | pyrrolidin-2-yl methyl | (2S) |
| 46 | 3-fluoro-phenyl | O | 4-methoxy | H | pyrrolidin-2-yl methyl | (2S) |
| 47 | 3-fluoro-phenyl | S | 4-methoxy | H | pyrrolidin-2-yl methyl | (2S) |
| 48 | pyridin-3-yl | NH | 4-methoxy | H | pyrrolidin-2-yl methyl | (2S) |
| 49 | 3-fluoro-phenyl | NH | 4-methoxy | H | pyrrolidin-2-yl methyl | (2S) |
| 50 | thiazol-2-yl | NH | 4-methoxy | H | pyrrolidin-2-yl methyl | (2S) |
| 51 | 3-chloro-phenyl | O | 4-methoxy | H | pyrrolidin-2-yl methyl | (2S) |
| 52 | 3-methoxy-phenyl | O | 4-methoxy | H | pyrrolidin-2-yl methyl | (2S) |
| 53 | 3-cyano-phenyl | O | 4-methoxy | H | pyrrolidin-2-yl methyl | (2S) |
| 54 | 3,5-difluoro-phenyl | O | 4-methoxy | H | pyrrolidin-2-yl methyl | (2S) |

Biological Examples

In Vitro Assays

Example 1

NG108-15, 24-Well Delta Opioid Receptor Binding Assay

Methods: NG108-15 cell membranes were purchased from Applied Cell Sciences (Rockville, Md.). 5 mg/mL of membrane protein was suspended in 10 mM TRIS-HCl pH 7.2, 2 mM EDTA, 10% sucrose. With several brief pulses from a Polytron homogenizer, each vial was homogenized in 5 mls of 50 mM Tris Buffer, pH 7.4. The homogenate was diluted in 50 mM Tris Buffer containing 5 mM $MgCl_2$ to 330 ug/ml in the working solution for a final concentration of 133 ug/well. This particulate preparation was used for the 24-well delta opioid binding assay.

Following incubation with the delta selective ligand ~0.2 nM [$^3$H]Naltrindole at 25° C. for 2.5 h in a 24-well plate with total volume of 1 mL, the plate contents were filtered through a UniFilter24, GF/B. This plate was presoaked in 0.3% PEI and filtered through a 24-well Harvester. The UniFilter24 was rinsed three times with 2 mL of 10 mM HEPES (pH 7.4), and dried in an oven at 37° C. for 1.5 hours. To each well, was added 150 µL of Scint0 (PerkinElmer, Cat#6013611). The plates were then read on a TopCount.

Analysis: The data from the scintillation counter were used to calculate either the % inhibition compared to control binding (when only a single concentration of test compound was evaluated) or a $K_i$ value (when a range of concentrations was tested). Non-specific binding (N.S.-1 mM Naloxone) is used as the negative control, while the Total Binding (T.B.-Membrane and ligand only) is used as the positive control. If one concentration is screened, the % inhibition is calculated as (cpms of total binding minus cpms of compound) divided by (cpms of T.B.minus cpms of N.S). The triplicate % Inhibitions are averaged and reported. If multiple concentrations are generated, the values are analyzed using the one-site binding non-linear regression program in Prism to determine Ki values. The bottom and top values are globally shared. The triplicate Kis are then averaged and reported.

The data obtained are shown in Table 2, below.

Example 2

Rat Brain Delta Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the delta selective peptide ligand ~4 nM [$^3$H]DPDPE or 0.25 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 µL of Betaplate Scint scintillation fluid (LKB) was added and the radioactivity was quantified on a LKB (Wallac) 1205 BetaPlate liquid scintillation counter.

Analysis: The data from the scintillation counter was used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program. The data obtained are shown in Table 2, below.

Example 3

Rat Brain Mu Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the mu opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 µL of Betaplate Scint scintillation fluid (LKB) was added and the radioactivity was quantified on a LKB (Wallac) 1205 BetaPlate liquid scintillation counter.

Analysis: The data from the scintillation counter was used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program. The data obtained are shown in Table 2, below.

TABLE 2

Delta and Mu Opioid Receptor Binding Data

| Cpd No. | δ-binding NG108 cell membrane $K_i$ (µM) | δ-binding (DPDPE ligand) $K_i$ (µM) | δ-binding (Naltrindole ligand) $K_i$ (µM) | µ-binding $K_i$ (µM) |
|---|---|---|---|---|
| 1 | | | 0.00590 | 3.883 |
| 2 | | | 0.00761 | 2.440 |
| 3 | | | 0.0161 | 1.667 |
| 4 | | | 0.0163 | 4.420 |
| 5 | | | 0.0183 | 0.0182 |
| 6 | | | 0.0437 | 1.836 |
| 7 | | | 0.0684 | 2.848 |
| 8 | | | 0.0925 | 7.163 |
| 9 | | | 0.115 | 9.289 |
| 10 | | | 0.130 | >10 |
| 11 | | | 0.155 | 2.151 |
| 12 | | | 0.174 | 15.226 |
| 13 | | | 0.238 | >10 |
| 14 | | | 0.254 | >10 |
| 15 | | | 0.297 | 3.235 |
| 16 | | | 0.455 | 3.864 |
| 17 | | | 0.477 | 12.316 |
| 18 | | 0.117 | | >10 |
| 19 | | 0.232 | | 2.054 |
| 20 | | 0.274 | | >10 |
| 21 | | 0.348 | | >10 |
| 22 | | 0.357 | | 9.283 |
| 23 | | 0.363 | | >10 |
| 24 | | 0.396 | | >10 |
| 25 | | 0.489 | | 2.508 |
| 26 | | | 0.885 | 8.782 |
| 27 | | | 1.015 | 3.575 |
| 28 | | | 1.530 | >10 |
| 29 | | | 1.874 | 162.70 |
| 30 | | | 1.956 | >10 |
| 31 | | 0.723 | | >10 |
| 32 | | 0.876 | | >10 |
| 33 | | 1.112 | | >10 |
| 34 | | 1.117 | | >10 |
| 35 | | 1.431 | | >10 |
| 36 | | | 2.135 | >10 |
| 37 | | | 2.702 | >10 |
| 38 | | | 3.088 | >10 |
| 39 | | | 3.526 | >10 |
| 40 | | | 4.366 | >10 |
| 41 | | | 5.325 | >10 |
| 42 | | 3.812 | | >10 |
| 43 | | 4.216 | | >10 |
| 45 | 0.00145 | | | |
| 46 | 0.000288 | | | |
| 47 | 0.000739 | | | |

Example 4

[$^{35}$S]GTPγS Binding Assay in NG108-15 Cell Membranes (Delta Opioid Functional Assay)-200 nM Screen Methods: NG108-15 cell membranes were purchased from Applied Cell Sciences (Rockville, Md.). 5 mg/mL of membrane protein was suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM $MgCl_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL assay buffer was added into the pellet containing tube. The pellet and buffer were mixed with a Polytron.

Incubation procedure: The pellet membranes (75 µg/mL) were preincubated with SPA (10 mg/mL) at 25° C. for 45 min in the assay buffer. The SPA (5 mg/mL) coupled with membranes (37.5 µg/mL) was then incubated with 0.1 nM [$^{35}$3] GTPγS in the same Tris buffer containing 100 µM GDP in total volume of 200 µL. 200 nM of receptor agonists was used to stimulate [$^{35}$3]-GTPγS binding. The basal binding was tested in the absence of agonists and non-specific binding was tested in the presence of 10 μM unlabeled GTPγS. The data were analyzed on a Packard Top Count and are shown in Table 3, below.

Data

% of Basal=(stimulated−non specific)*100/(basal−non specific).

Relative Efficacy of a compound at 200 nM=(% of Basal of test compound at 200 nM)/(Calculated Max of SNC80 dose response. Curve in prism).

Example 5

[$^{35}$S]GTPγS Binding Assays in CHO-hMOR Cell Membranes (mu Opioid Functional Assay)

Methods: CHO-hMOR cell membranes can be purchased from Receptor Biology, Inc. (Baltimore, Md.). About 10 mg/mL of membrane protein can be suspended in 10 mM TRIS-HCl pH 7.2, 2 mM EDTA, 10% sucrose, and the suspension kept on ice. A 1 mL volume of membranes can be added to 15 mL cold binding assay buffer containing 50 mM HEPES, pH 7.6, 5 mM MgCl$_2$, 100 mM NaCl, 1 mM DTT and 1 mM EDTA. The membrane suspension can be homogenized with a Polytron and centrifuged at 3,000 rpm for 10 min. The supernatant can then be centrifuged at 18,000 rpm for 20 min. The pellet can be resuspended in 10 mL assay buffer with a Polytron. The membranes can be preincubated with wheat germ agglutinin coated SPA beads (Amersham) at 25° C. for 45 min in the assay buffer. The SPA bead (5 mg/mL) coupled membranes (10 μg/mL) can be then incubated with 0.5 nM [$^{35}$S]GTPγS in the assay buffer. The basal binding can be that taking place in the absence of added test compound; this unmodulated binding can be considered as 100%, with agonist stimulated binding rising to levels significantly above this value. A range of concentrations of receptor agonist can be used to stimulate [$^{35}$S]GTPγS binding. Both basal and non-specific binding can be tested in the absence of agonist; non-specific binding determination included 10 μM unlabeled GTPγS.

Compounds can be tested for function as antagonists by evaluating their potential to inhibit agonist-stimulated GTPγS binding. Radioactivity can be quantified on a Packard Top-Count. The following parameters can be calculated:

$$\% \text{ stimulation} = \frac{(\text{test compound cpm} - \text{non-specific cpm})}{(\text{basal cpm} - \text{non-specific cpm})} \times 100.$$

$$\% \text{ inhibition} = \frac{\left(\begin{array}{c}\% \text{ stimulation by 1 μM DAMGO} - \\ \% \text{ stimulation by test compound}\end{array}\right)}{(\% \text{ stimulation by 1 μM DAMGO} - 100)} \times 100$$

EC$_{50}$ values can be calculated using GraphPad Prism and are shown in Table 3, below.

TABLE 3

Delta and Mu Opioid Receptor Functional Data

| Cpd No. | GTPγS δ-Rel Efficacy @200 nM | GTPγS δ-opioid receptor EC$_{50}$ (μM) | GTPγS δ-opioid receptor % Inh @10 μM | GTPγS δ-opioid receptor Rel Efficacy | GTPγS μ-opioid receptor EC$_{50}$ (μM) | GTPγS μ-opioid receptor % Inh @10 μM |
|---|---|---|---|---|---|---|
| 1 | | 0.812 | 17.499 | 0.664 | 84.334 | 19.461 |
| | | 3.653 | 16.430 | | | |
| 2 | | 0.828 | 8.163 | | | |
| 3 | | 0.559, | 12.801 | 1.106 | | |
| | | 0.092, | 19.733 | | | |
| | | 0.206 | | | | |
| 4 | | 1.030 | 8.936 | 0.923 | | |
| 5 | | 2.622 | 26.400 | 0.471 | | |
| 6 | | | 12.502 | | | |
| 7 | | 0.221 | 20.645 | | | |
| 44 | | 1.110 | 15.636 | | | |
| 45 | | 0.734 | | 1.178 | | |
| 46 | 0.770 | 0.028 | | 0.983 | | |
| 47 | 0.481 | 0.193 | | 1.079 | | |
| 48 | 0.267 | | | | | |
| 49 | 0.216 | | | | | |
| 50 | 0.143 | | | | | |
| 51 | 0.859 | 0.043 | | 1.040 | | |
| 52 | 0.624 | 0.051 | | 0.935 | | |
| 53 | 0.705 | 0.053 | | 1.033 | | |
| 54 | 0.066 | | | | | |

In Vivo Assay

Example 6

Rat CFA Radiant Heat Model of Inflammatory Pain

Intraplantar injection of Complete Freund's Adjuvant (CFA) in rodents results in a strong, long-lasting inflammatory reaction, characterized by a chronic and pronounced hyperalgesia to both thermal and mechanical stimuli. These effects peak between 24-72 h following injection, and can last for several days to a few weeks. To assess the ability of compounds to reverse thermal hyperalgesia, male Sprague-Dawley rats (200-350 g) may be given an intraplantar injection of CFA (1:1 CFA:saline, 100 μL) into their left hindpaw. Following a 24-h incubation period, response latencies on the Radiant Heat Paw Stimulator (RH) may be obtained and compared to baseline (pre-CFA) latencies. The RH device automatically registers lifting of the paw from the surface of the glass. Only rats that exhibit at least a 25% reduction in response latency from baseline (i.e. hyperalgesia) are included in further analysis. Following the post CFA latency assessment, rats may be dosed orally (2.5 mL/kg) with test compound or vehicle (hydroxypropylmethylcellulose, HPMC). Percent reversal of hyperalgesia may be calculated for each animal as (Treatment Response−postCFA Response)/(preCFA Response−postCFA Response)×100. Therefore, a return to normal pre-CFA thresholds may be defined as 100% efficacy, whereas no change from post-CFA thresholds may be 0% efficacy. Average % reversal of hyperalgesia may be calculated for each treatment group (n=6-8 rats/group).

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for treating mild to severe pain in a subject in need thereof, comprising administering to the subject a therapeutically effective amount of a compound of Formula I

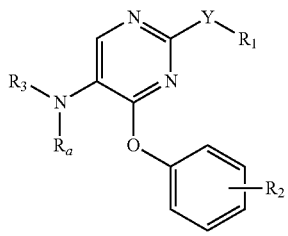

Formula I wherein
- R₁ is selected from the group consisting of phenyl, pyridinyl, and thiazolyl; wherein R₁ is optionally substituted with one to two substituents independently selected from the group consisting of $C_{1-4}$alkyl, $C_{1-4}$alkoxy, $C_{1-4}$alkylthio, hydroxy, fluoro, chloro, bromo, and cyano; in addition, R₁ is optionally substituted with amino, $C_{1-4}$alkylamino, di($C_{1-4}$alkyl)amino, aminocarbonyl, $C_{1-4}$alkylaminocarbonyl, or di($C_{1-4}$alkyl)aminocarbonyl;
- Y is O, S, NH, vinyl, ethynyl or S(O);
- R₂ is a substituent selected from the group consisting of hydrogen, $C_{1-4}$alkyl, $C_{1-4}$alkoxy, $C_{1-4}$alkylthio, fluoro, chloro, bromo, and hydroxy;
- $R_a$ is hydrogen or methyl;
- R₃ is selected from the group consisting of pyrrolidin-2-ylmethyl, pyrrolidin-3-ylmethyl, piperidin-2-ylmethyl, piperidin-3-ylmethyl, piperidin-4-ylmethyl, piperidin-2-ylethyl, piperidin-3-ylethyl, piperidin-4-ylethyl, pyridin-4-yl-($C_{1-2}$)alkyl, azetidin-3-ylmethyl, morpholin-2-ylmethyl, morpholin-3-ylmethyl, imidazolylmethyl, thiazolylmethyl, (amino)-$C_{3-6}$cycloalkyl, 3-hydroxy-2-amino-propyl, 8-aza-bicyclo[3.2.1]octanyl, 1-aza-bicyclo[2.2.2]octanyl, guanidinyl-ethyl, 4-(imidazol-1-yl)-phenylmethyl, 2-(methylamino)-ethyl, 2-diethylamino-ethyl, 4-diethylamino-but-2-yl, piperidin-3-yl, piperidin-4-yl, and pyrrolidin-3-yl;
- and wherein piperidin-3-yl is optionally substituted at a carbon atom with phenyl; and wherein pyrrolidin-2-yl of pyrrolidin-2-ylmethyl, pyrrolidin-3-yl, piperidin-3-yl, and piperidin-4-yl are optionally substituted at a nitrogen atom with methyl, phenylmethyl, phenethyl, or methylcarbonyl;
- and enantiomers, diastereomers, and pharmaceutically acceptable salts thereof.

2. The method of claim 1 wherein the mild to severe pain is due to a disease or condition selected from the group consisting of osteoarthritis, rheumatoid arthritis, fibromyalgia, migraine, headache, toothache, burn, sunburn, snake bite, spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulitis, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

3. The method of claim 1 wherein the pain is selected from the group consisting of inflammatory pain, centrally mediated pain, peripherally mediated pain, visceral pain, structural related pain, cancer pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine.

* * * * *